United States Patent [19]
Dougherty et al.

[11] Patent Number: 5,906,928
[45] Date of Patent: May 25, 1999

[54] EFFICIENT GENE TRANSFER INTO PRIMARY MURINE LYMPHOCYTES OBVIATING THE NEED FOR DRUG SELECTION

[75] Inventors: Joseph Dougherty, Hampton; Yacov Ron, East Brunswick, both of N.J.

[73] Assignee: University of Medicine and Dentistry of New Jersey, Newark, N.J.

[21] Appl. No.: 08/586,754

[22] PCT Filed: Aug. 1, 1994

[86] PCT No.: PCT/US94/08612

§ 371 Date: Mar. 19, 1996

§ 102(e) Date: Mar. 19, 1996

[87] PCT Pub. No.: WO95/07358

PCT Pub. Date: Mar. 16, 1995

Related U.S. Application Data

[63] Continuation-in-part of application No. 08/100,546, Jul. 30, 1993, abandoned.

[51] Int. Cl.⁶ .......................... C12N 15/10; C12N 15/63; C12N 15/86; C12N 5/10
[52] U.S. Cl. ..................... 435/172.3; 435/320.1; 435/355; 435/357; 435/372; 435/372.2; 435/372.3; 435/373
[58] Field of Search ................. 435/5, 6, 172.3, 435/320.1, 240.2, 355, 357, 372, 373, 372.2, 372.3, 366, 354, 235.1

[56] References Cited

U.S. PATENT DOCUMENTS

| | | | |
|---|---|---|---|
| 4,650,764 | 3/1987 | Temin et al. | 435/240.2 |
| 4,980,289 | 12/1990 | Temin et al. | 435/235.1 |
| 5,124,263 | 6/1992 | Temin et al. | 435/240.2 |
| 5,399,346 | 3/1995 | Anderson et al. | 424/93.21 |

FOREIGN PATENT DOCUMENTS

| | | |
|---|---|---|
| WO 89/11539 | 11/1989 | WIPO . |
| WO 93/07281 | 4/1993 | WIPO . |

OTHER PUBLICATIONS

Sutkowski et al., 1994, Proc. Natl. Acad. Sci. USA 91:8875–79.
Sprent and Tough, 1994, Science 265: 1395–99.
Tough and Sprent, 1994, J. Exp. Med. 179: 1127–35.
Kuo et al., 1993, Blood 82:845–52.
Sutkowski et al., 1993, J. Cell. Biochem. Suppl. 17B: 166.
Braakman et al., 1992, Eur. J. Immunol. 22: 63–69.
van Beusechem et al., 1992, Proc. Natl. Acad. Sci. USA 89: 7640–44.

(List continued on next page.)

*Primary Examiner*—David Guzo
*Attorney, Agent, or Firm*—Klauber & Jackson

[57] ABSTRACT

The present invention pertains to a method for efficiently introducing exogenous genes into primary lymphoid cells without drug selection which comprises the steps (a) deriving a retroviral vector and a helper cell combination that will yield a level of virus production in the range from $5 \times 10^6$ to $5 \times 10^7$ units/ml by transfecting a vector into a helper cell followed by selection, isolation of cell clones, and determination of viral titers to identify which virus-producing cell lines produce a virus titer in the range from $5 \times 10^6$ to $5 \times 10^7$ units/ml; (b) isolating a lymphoid cell subpopulation which can repopulate a specific lymphoid lineage or is a long-lived population by treating a suspension of lymphoid cells with a monoclonal antibody which removes undesired lymphoid cells to obtain an enriched lymphoid subpopulation; (c) culturing the enriched lymphoid subpopulation from step (b) with growth factors specific to the lymphoid subpopulation; (d) co-cultivating the lymphoid subpopulation from step (c) with a lawn of irradiated virus-producing cell line from step (a) to produce an infected lymphoid subpopulation; and (e) harvesting the infected lymphoid subpopulation. The invention further relates to a population of transfected lymphocytes, in which greater than about 90% of the lymphocytes contain a provirus.

30 Claims, 9 Drawing Sheets

OTHER PUBLICATIONS

Malim et al., 1992, J. Exp. Med. 176: 1197–1201.
Riddell et al., 1992, Science 257:238–41.
Zimmermann et al., 1992, Human Gene Therapy 3: 155–61.
Culver et al., 1991, Human Gene Therapy 2: 107–109.
Culver et al., 1991, Proc. Natl. Acad. Sci. USA 88: 3155–59.
Fauser, 1991, J. Cell. Bioch. 45:353–58.
Ferrari et al., 1991, Science 251: 1363–66.
Greenberg, 1991, Adv. Immunol. 49: 281–355.
Krauss et al., 1991, Human Gene Therapy 2: 221–28.
Lupton et al., 1991, Mol. Cell. Biol. 11: 3374–78.
Sprent et al., 1991, J. Exp. Med. 174: 717–28.
Kasid et al., 1990, Proc. Natl. Acad. Sci. USA 87: 473–77.
Wilson et al., 1990, Proc. Natl. Acad. Sci. USA 87: 439–43.
Bender et al., 1989, Mol. Cell. Biol. 9: 1426–34.
Bodine et al., 1989, Proc. Natl. Acad. Sci. USA 86: 8897–8901.
Lim et al., 1989, Proc. Natl. Acad. Sci. USA 86: 8892–96.
Szilvassy et al., 1989, Proc. Natl. Acad. Sci. USA 86: 8798–8802.
Markowitz et al., 1988, J. Virol. 62: 1120–24.
Lemischka et al., 1986, Cell 45: 917–27.
Reimann et al., 1986, J. Immunol. Methods 89: 93–101.
Uchida et al., 1986, J. Immunol. 136: 1876–79.
Kantoff et al., 1986, Proc. Natl. Acad. Sci USA 83: 6563–67.
Richter et al., 1984, Mol. Cell. Biol. 4: 151–59.
Mann et al., 1983, Cell 33: 153–59.
Miller, Nature, vol. 357, Jun. 11, 1992, pp. 455–460.
Finer et al., Blood, vol. 83, No. 1, Jan. 1, 1994, pp. 43–50.

3.7 Kbp

— human
— mouse 3.7 kbp -

FIG. 8

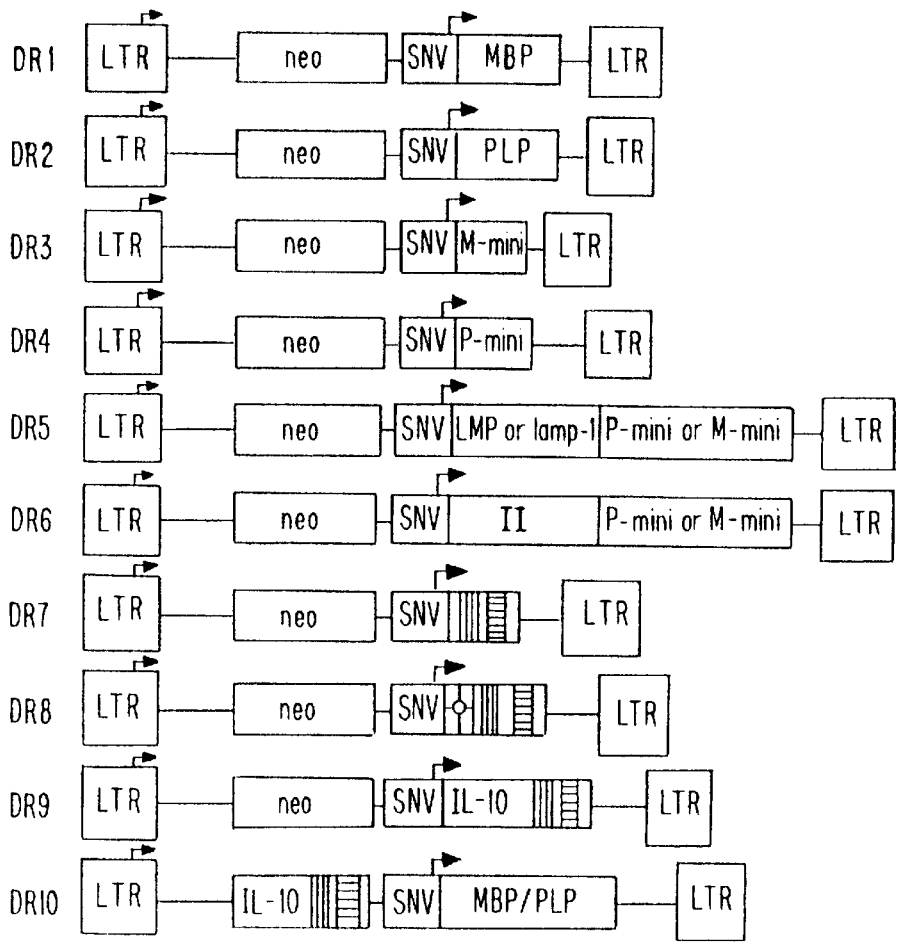

- LTR - long terminal repeat
- SNV - spleen necrosis virus promoter
- neo - neomycin phosphotransferase gene
- —— - vector viral sequences
- ▶ - size of transcription initiation
- MSP - myelin basic protein gene
- PLP - proteolipid protein gene
- M-mini - portion of the MBP gene containing the encephalogenic determinant and some flanking sequences
- P-mini - portion of the PLP gene containing the encephalogenic determinant and some flanking sequences
- LMP - cytoplasmic tail of lysosomal acid phosphatase
- lamp-1 - cytoplasmic tail of lysosomal membrane protein
- II - MHC class II-associated invariant chain gene
- ▦ - two ribozymes targeting both B7 RNAs
- ⦵ - stem-loop structure which inhibits translation
- IL-10 - interleukin 10 gene
- MBP/PLP - gene encoding MBP or PLP encephalogenic determinant in the form that is most efficiently presented by MHC Class II

EFFICIENT GENE TRANSFER INTO PRIMARY MURINE LYMPHOCYTES OBVIATING THE NEED FOR DRUG SELECTION

This application is a 371 application of PCT/US94/08612, filed Aug. 1, 1994 and is a continuation-in-part of Ser. No. 08/100,546, filed Jul. 30, 1993, now abandoned.

The research leading to the present invention was supported in part by National Institutes of Health Grant 5 R29 CA50777-03, and National Institutes of Health Research Services Award 1T32 A107043-01. The Government may have certain rights in the invention.

FIELD OF THE INVENTION

The present invention relates to a method for efficiently introducing exogenous genes into lymphoid cells using retroviral vectors and helper cells. The gene transfer method of the present invention is achieved without drug selection and is potentially important for somatic cell gene therapy and for studying lymphocyte biology.

BACKGROUND OF THE INVENTION

The disclosures referred to herein to illustrate the background of the invention and to provide additional detail with respect to its practice are incorporated herein by reference. For convenience, the disclosures are referenced in the following text and respectively grouped in the appended bibliography.

Retroviral vectors are the most efficient tools for the stable introduction of genes into vertebrate cells. Clinical experiments have been conducted to use retrovirus vectors to cure a genetic disease in humans (adenosine deaminase (ADA) deficiency). Besides correcting inborn errors of metabolism, gene therapy is also being tested in clinical trials to cure cancer and various other diseases (Science 1992, Vol. 258, pp. 744–746).

Retroviral vectors are basically retroviral particles that contain a crippled viral genome in which all viral protein coding sequences have been replaced with the gene(s) of interest. As a result, such viruses cannot further replicate after one round of infection without the help of a helper virus. Retroviral vector particles are produced by helper cells. Such helper cells contain plasmid constructs which express all retroviral proteins necessary for particle production and replication. After the introduction (transfection) of the retroviral vector genome into such helper cells, the vector genome (an RNA genome) is encapsulated into virus particles (due to the presence of specific encapsidation sequences). Virus particles are released from the helper cell carrying a genome containing only the gene(s) of interest. After infection of a fresh target cell, the RNA genome is reverse transcribed into DNA and the DNA copy is integrated into the host genome. The integrated viral DNA is called the provirus. In the last decade, several retroviral vector systems, derived from chicken or murine retroviruses, have been developed for the expression of various genes (for reviews see Temin, 1987; Gilboa, 1990).

Efficient Gene Transfer into Primary Murine Lymphocytes

Much attention has been focused upon experimental animal models aimed at the efficient introduction of exogenous genes into hematopoietic stem cells using retroviral vectors (Williams et al., 1984, Nature 310:476; Dzierzak et al., 1989, Nature 331:35; Bender et al., 1989, Mol. Cell Biol. 9:1426). The ability of pluripotential stem cells to repopulate all hematopoietic cell lineages, and their capacity for self-renewal (Williams et al., 1984, Nature 310:476; Lemischka et al., 1986, Cell 45:917) make them attractive target cells to correct genetic defects affecting hematopoietic cells (Parkman, 1986, Science 232:1373). Technically, however, this has proven somewhat difficult, primarily because whole bone marrow contains very few pluripotential stem cells and as yet, no unique cell surface markers have been identified on these cells making it difficult to purify sufficient quantities for detailed analysis. Thus, gene transfer into these cells has been inefficient (Szilvassy et al., 1989, Proc. Natl. Acad. Sci. USA 86:8798) and even when transfer has been achieved, appropriate expression of the transferred gene has often been problematic, possibly because pluripotential stem cells undergo many differentiation steps before reaching maturity which might interfere with the proper expression of the introduced gene. It has therefore been suggested that for certain diseases which effect the lymphoid compartment, or which might be treated by augmenting immune responses, gene transfer into primary lymphocytes might be helpful, and in some cases preferred (Culver et al., 1991, Proc. Natl. Acad. Sci. USA 88:3155; Culver et al., 1991, Human Gene Therapy 2:107). Primary lymphocytes are easy to obtain; many of them are long-lived; and they can be easily induced to proliferate, a required step for infection using retroviral vectors (Richter et al., 1984, Mol. Cell Biol. 4:151). Such advantages have thus recently motivated research on gene transfer into primary lymphocytes.

Murine Model for B Cell Lineage Somatic Cell Gene Therapy

The efficient transfer of exogenous genes into primary B lymphocytes has direct therapeutic potential for the treatment of diseases that affect the B cell compartment such as X-linked agammaglobulinemia (Vetrie et al., 1993, Nature 361:226; Tusukada et al., 1993, Cell 72:279) and ADA deficiency (Anderson, 1992, Science 256:808). It also has therapeutic potential for genetic diseases in which delivery of a normal gene product into the blood stream can be helpful, such as in hemophilia (factor VIII and factor IX deficiency) (Miller, 1990, Blood 76:271; Hoeben et al., 1992, Thromb. Haemost. 67:341; Hoeben et al., 1993, Hum. Gene Ther. 4:179) and lipoprotein lipase deficiency (Hayden & Ma, 1992, Mol. Cell. Biochem. 113:171; Auwerx et al., 1992, Critical Reviews in Clinical Laboratory Sciences 29:243). Furthermore, since B cells function as antigen presenting cells, they can be manipulated to express tumor or viral antigens to initiate or augment anti-tumor or anti-viral immune responses. An additional advantage of using B cells as targets is the fact that much is known about the regulation of expression of immunoglobulin heavy and light chain genes. This information could be used to optimize tissue-specific expression of exogenous genes in B cells. Moreover, the immunoglobulin secretory pathway could be utilized for the secretion of large quantities of an exogenous gene product.

Several gene therapy protocols involving retroviral-vector-mediated transfer of exogenous genes into lymphocytes are in clinical trials. These include the introduction of the adenosine deaminase (ADA) gene into peripheral blood T cells of ADA deficient, severe combined immunodeficiency (SCID) patients (Sprent, 1973, Cell. Immunol. 7:10; Stevens et al., 1982, J. Immunol. 128:844), and the introduction of marker genes or lymphokine genes into tumor infiltrating (TIL) T cells (Kasis et al., 1990, Proc. Natl. Acad.

Sci. U.S.A. 87:473; Culver et al., 1991, ibid. 88:3155). These protocols rely on long-term in vitro expansion and/or drug selection of the target cells to enrich for stably infected cells. Since B cells cannot be efficiently expanded in vitro, these procedures are inadequate for the introduction of genes into B cells. Moreover, cells from long-term cultures usually result in altered homing patterns and do not home properly into lymphoid organs upon adoptive transfer (Dailey et al., 1985, J. Mol. Cell. Immunol. 2:27; Tedder et al., 1990, J. Immunol. 144:532; Kishimoto et al., 1990, Proc. Natl. Acad. Sci. U.S.A. 87:2244).

Multiple Sclerosis

Multiple Sclerosis (MS) is a chronic inflammatory disease of the CNS associated with "plaque-like" areas of demyelination mainly in perivascular areas within the white matter. The permeability of the blood-brain barrier to small molecules and cells is increased in MS and plaques are infiltrated by leukocytes, predominantly lymphocytes an macrophages. Very histological and clinical signs characterize the experimental disease EAE (Sobel et al., 1984, J. Immunol. 132:2393; Sedgwick et al., 1987, J. Exp. Med. 165:1058), and is considered the experimental model best approximating MS. However, certain important differences do exist between MS and EAE particularly in the clinical course. MS is characterized by exacerbations and remission of neurologic dysfunctions but with clear progression of the severity of relapse episodes. EAE, on the other hand, is usually a monophasic, acute illness associated with complete recovery and immunity to subsequent challenges. Recently, however, experimental protocols to induce a more chronic, relapsing form of EAE in mice were developed. A chronic disease is usually achieved in a substantial percentage of animals injected with presensitized T cells, by alterations of the host immune system and by some induction protocols using conventional MBP/CFA injections (Fallis and McFarland, 1989, J. Immunol. 143:2160; Lassmann and Wisniewski, 1979, Acta. Neuropathol. 47:111; Brown and McFarlin, 1981, J. Lab. Invest. 45:278; Ben-Nun et al., 1980, Nature 288:389; Lublin et al., 1981, J. Immunol. 126:819; Fritz et al., 1983, J. Immunol. 130:1024; Mokhtarian et al., 1984, Nature 309:356; Zamvil et al., 1985, Nature 317:355; Fallis et al., 1989, J. Neuroimmunol. 22:93).

Another often criticized aspect of using EAE as a model for MS has been the difficulty of isolating MBP-reactive T cells from the peripheral blood and cerebrospinal fluid (CSF) of MS patients. Many recent reports have shown that this, in fact, is not the case. MBP-specific, class-II restricted CF4+ T cells with a restricted T cell receptor usage have been isolated and propagated from cerebrospinal fluid and peripheral blood. Perhaps the best illustration of the relevance of EAE research to MS are the therapeutic protocols derived from experiments initiated in mice some of which are currently clinical trials in humans. Developing strategies for preventing EAE induction and/or relapse is important for developing treatments for MS.

The citation of any reference herein should not be construed as an admission that such reference is available as prior art to the instant invention.

BRIEF DESCRIPTION OF THE FIGURES

FIG. 2(A) is a Southern blot of N2-infected cells and FIG. 2(B) is a Southern blot of AsADA-infected cells.

FIG. 3 shows gene transfer and expression in lymph node T cells.

FIG. 4 shows gene transfer and expression in lymph node B cells.

FIG. 8 shows a schematic of murine-leukemia virus vectors that for expression of autoantigens associated with experimental autoimmune encephalomyelitis (EAE), an animal model for multiple sclerosis (MS), in order to induce non-responsiveness to the autoantigens.

SUMMARY OF THE INVENTION

Figure 1:
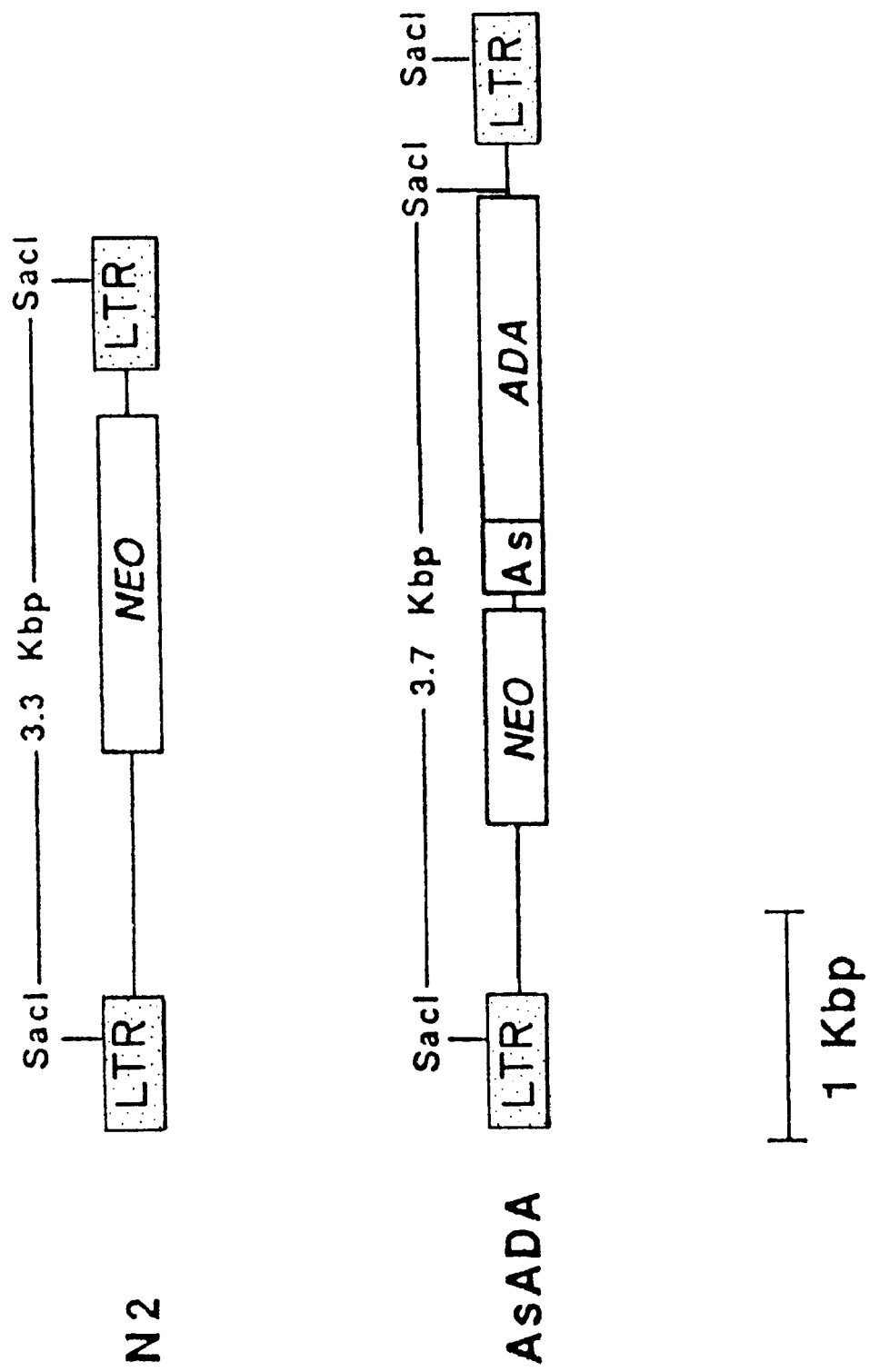
FIG. 1 illustrates schematically the retroviral vectors of the present invention. N2 and AsADA are Moloney murine leukemia virus-based vectors. N2 contains the neomycin phosphotransferase II gene (neo), expressed from the viral long terminal repeat (LTR) promoter. AsADA contains neo, expressed from the viral LTR promoter, and the human adenosine deaminase gene (ADA), expressed from its endogenous promoter (As).

The present invention pertains to a method for efficiently introducing exogenous genes into primary lymphoid cells without drug selection. The invention comprises the steps of stimulating a selected lymphoid subpopulation with growth factors that induce proliferation of the lymphoid subpopulation for a time sufficient to induce proliferation of the lymphoid subpopulation, and co-culturing the stimulated lymphoid subpopulation with a virus-producing helper cell line, wherein the level of virus production of the helper cell line is in the range from $5\times10^6$ to $5\times10^7$ colony forming units/ml.

Such retroviral vectors are available in the art, or may be prepared by following standard protocols. For example, such helper (or producer) cell lines can be formed by transfecting a vector into a helper cell followed by selection, isolation of cell clones, and determination of viral titers to identify which virus-producing cell lines produce a virus titer in the range from $5\times10^6$ to $5\times10^7$ units/ml.

Preferably, the selected lymphoid subpopulation is isolated, e.g., by depleting undesired cells from the population. Depletion of undesired cells can be achieved by treating a suspension of lymphoid cells with a polyclonal or a monoclonal antibody and complement, by panning, by nylon wool selection, by differential gradient centrifugation, or any technique that removes undesired lymphoid cells to obtain an enriched lymphoid subpopulation. Such a lymphoid subpopulation may be capable of repopulating a specific lymphoid lineage, or may be a long-lived population.

After the co-cultivation is complete, the transfected lymphoid cells may be harvested.

DETAILED DESCRIPTION OF THE INVENTION

The present invention relates to a method for efficiently introducing exogenous genes into lymphoid cells such as primary, mature murine lymph node T and B cells, and primary, immature murine $CD4^-CD8^-$ double-negative (DN) thymocytes using retroviral vectors. The novel gene transfer method provides for (a) the generation of helper cells that produce very high titers of the retroviral vector carrying the exogenous gene, (b) the isolation of lymphoid subpopulations which can either repopulate a specific lymphoid lineage, in the case of progenitor cells, or is a long-lived population, in the case of mature lymphocytes, and (c) the efficient and rapid introduction of the exogenous gene into the target cell population.

To achieve the efficient selection procedures of the invention, ector-producing helper cell lines can be cloned that produce virus titers from $5 \times 10^6$ to $5 \times 10^7$ units/ml. The present method also includes purification protocols for lymphoid progenitor cells which upon introduction into SCID or lethally irradiated hosts will repopulate the B cell or the T cell lineages. Purification protocols have also been developed for mature B cell or T cell subpopulations which will survive for prolonged periods upon adoptive transfer into SCID or normal hosts. The protocol is very fast and efficient with over 90% of the target cells successfully infected with from 1 to 5, preferably from 1 to 3, proviruses, within about 24 to 40 hours. These advantages are significant for gene therapy because they eliminate the selection step used by current protocols to enrich for target cells that express the desired gene and therefore shorten the period the target cells are manipulated in vitro which greatly improves the proper homing of the cells once introduced back into the host. The novel gene transfer method allows for the potential correction of genetic disorders originating from genetic defects in lymphocytes and also for the correction of other genetic disorders in which a missing gene product may be supplied systemically by lymphocytes.

One aspect of the method involves determining which retroviral vector and helper cell combination will yield a high level of virus production, i.e., $5 \times 10^6$ to $5 \times 10^7$ units/ml. In this vector-producing helper cell line selection procedure, a vector is transfected into a helper cell followed by selection, isolation of cell clones, and determination of viral titers to identify which virus-producing cell lines produce a virus titer in the range from $5 \times 10^6$ to $5 \times 10^7$ units/ml.

According to the invention, many of the producer cell line-vector combinations known in the art can be used to practice the instant invention. Generally, a vector is transfected into a helper cell line. Cell lines that produce about $5 \times 10^5$ c.f.u./ml are selected. Subcloning of these cell will yield a line that is capable of producing up to $10^7$ c.f.u./ml of virus.

In a specific embodiment, infra, for gene transfer into murine lymphoid cells, the cell line is the GP+E-86 cell line (Elwood et al., 1994, Leukemia 8:106–114; Matsushita et al., 1993, Thrombosis Res. 69:387–393; Wilson et al., 1993, Human Gene Therapy 4:25–34; Markowitz et al., 1990, Ann. N.Y. Acad. Sci. 612:407–414; Moore et al., 1990, Blood 75:2085–92), which is a NIH 3T3-based cell line, and the vector is selected from the group consisting of pN2 (Moore et al., 1991, Human Gene Therapy, 2:307–315; Alford and Belmont, 1990, Human Gene Therapy 1:269–276; Stoeckert et al., 1990, Experimental Hematology 18:1164–1170) and pAsADA, which are Maloney murine leukemia virus-based retroviral vectors that contain the neo gene under control of the MLV long terminal repeat promoter. In a specific embodiment, the vector encodes the human adenosine deaminase (ADA) gene under control of the endogenous promoter.

In another specific embodiment, for gene transfer into human lymphoid cells, the vector may be pMFG-NB (Ferry et al., Proc. Natl. Acad. Sci. USA 88:8377–81), and the helper cell may be prepared from the canine osteosarcoma cell line D17, which is available from the American Type Culture Collection (ATCC), accession number CCL183. The canine cell line can be prepared as a helper line according to known techniques (e.g., Pear et al., 1993, Proc. Natl. Acad. Sci. USA 90:8392–96; Miller et al., 1991, J. Virol. 65:2220–2224; Markowitz et al., 1988, Virol. 167:400–406; Markowitz et al., 1988, J. Virol. 62:1120–24; Danos and Mulligan, 1988, Proc. Natl. Acad. Sci. USA 85:6460–64; Dougherty et al., 1989, J. Virol. 63:3209, and U.S. Pat. No. 4,980,289 and U.S. Pat. No. 5,124,263 to Temin and Dougherty.

Another aspect of the present method involves isolating a lymphoid cell subpopulation which can repopulate a specific lymphoid lineage or is a long-lived population by treating a suspension of lymphoid cells with a monoclonal antibody which removes undesired lymphoid cells to obtain an enriched tymphoid subpopulation.

Yet another aspect of the present method involves the infection protocol. Appropriate growth factors are added to the particular type of lymphocytes to be infected to keep the cells proliferating. For mature B cells, lipopolysaccharides (LPS) may be used. For mature T cells, sequential treatment with concanavalin A and interleukin-2 may be used.

Preferably, the primary lymphocyte cells are stimulated for the length of time necessary to induce proliferation, e.g., about 24 hours. The stimulated lymphocytes are then co-cultivated with a lawn of helper (producer) cells, having a very high virus titer, in the presence of the growth factors. Preferably, the helper cells are irradiated. Irradiation stops the helper/producer cells from growing but still enables the cells to produce virus. Thus, the confluent lawn of producer cells does not overgrow the plate and lift off. The producer cells adhere to the plate and the lymphocytes do not. As the lymphocytes proliferate, a necessary step for virus integration, the lymphocytes become infected with the transgenic virus. The infected (or transfected) cells are then harvested and returned to the animal.

The vectors employed in the present invention have the sequences required in the genome for virus replication that must be covalently linked to the genome but do not have the sequences required for viral protein production. The vector has the cis acting sequences required for replication but not the trans acting sequences. The producer cell expresses virus protein but without producing virus (no genome which can be inserted into virus) and can therefore only produce empty particles. Vectors having straight LTR give higher virus titers.

Efficient Gene Transfer into Primary Lymphocytes

This invention relates to the use of retroviral vectors to efficiently introduce exogenous genes (approximately 1 to 5 copies per genome) into primary, mature lymph node T and B cells, and primary, immature CD4-CD8-double-negative (DN) thymocytes which contain precursor cells capable of reconstituting the entire T cell lineage (Nikolic-Zugic, 1991, Immunol Today). Efficient infection of primary cells is achieved by co-cultivation of target cells with lethally irradiated helper cells that produce high titers of retroviral vectors.

In a specific example, infra, helper/producer cells harboring retroviral vectors containing either the neomycin phosphotransferase II (neo) gene, or both the neo and the human adenosine deaminase (ADA) genes, were co-cultivated with isolated lymphocytes in the presence of lymphokines and/or mitogens. Two days post-infection, without neomycin selection, one to five copies of the exogenous genes per cell were detected by Southern blot analysis. Expression of the exogenous human ADA protein was detected at levels comparable to the endogenous murine ADA protein in the mature T and B lymphocytes, and was somewhat lower for the immature DN thymocytes. The infection protocol described here can be completed within 24 hours, hence it should be useful for in vivo animal reconstitution studies.

B Cell Lineage Somatic Cell Gene Therapy

Primary, mature B lymphocytes represent a potentially important cellular target for somatic cell gene therapy. Their capacity to serve as antigen presenting cells could be utilized for triggering and/or potentiating immune responses.

Alternatively, B cells expressing an autoantigen could be manipulated to induce antigen-specific unresponsiveness for treatment of autoimmune diseases. For example, the adoptive transfer of resting B cells expressing self-antigens could be used to confer antigen-specific unresponsiveness, as has been shown in other experimental systems. For example, the transfer of $Mls^a$ into $Mls^b$ mice was shown to induce clonal anergy and/or clonal deletion of host $Mls^a$-specific T cells (Rammensee et al., 1989, Nature 339:541–544; Webb et al., 1990, Cell 63:1249–56). This form of unresponsiveness is termed peripheral tolerance. As disclosed in an example, infra, peripheral tolerance may be especially powerful in autoimmune diseases, such as multiple sclerosis, and the animal model of MS, EAE, as well as rheumatoid arthritis, lupus, Sjogren's syndrome, and other autoimmune diseases. The invention accordingly contemplates that the induction of peripheral tolerance could prove to be a useful approach for treating T-cell mediated autoimmune diseases.

As discussed in the Examples, infra, vectors for transfection of an autoantigen in B cells can be prepared so that the autoantigen is expressed intracytoplasmically, for transport via the endogenous cellular machinery for presentation in the context of MHC class II molecules (e.g., Braciale and Braciale, 1991, Immunol. Today 12:124; Brodsky and Guagliardi, 1991, Ann. Rev. Immunol. 9:707). More preferably, the autoantigen can be expressed as a secreted protein or a cell surface protein, by including a signal sequence, and, in the latter case, a membrane-binding sequence. In another preferred embodiment, the autoantigen is expressed as a chimeric construct, with an endosomal or lysosomal targeting sequence at the cytoplasmic end (Braciale and Braciale, supra; Brodsky and Guagliardi, supra; Peters et al., 1990, EMBO J. 9:3497; Bakke and Dobberstein, 1990, Cell 63:707).

In a further aspect, vectors for inducing autoantigen-specific unresponsiveness can include antisense coding sequences for antigen presenting cell adhesion molecules, i.e., the molecules that facilitate binding to and stimulation of T cells. More preferably, the vector provides for expression of a ribozyme specific for such cell surface molecules. Co-expression of antisense RNA or ribozymes can further increase T cell anergy by decreasing the expression of cell surface accessory molecules that are important for stimulating T cells, and the immune response in general.

In yet another aspect, the vector can include a lymphokine or cytokine that inhibits T cell activation, such as, but not limited to, interleukin-10 (IL-10).

Long-lived B lymphocytes might also be useful for providing a corrected gene product into the blood stream.

In accord with the present invention, an animal model system is described for B lymphocyte gene therapy, which employs an efficient and rapid protocol for the introduction of exogenous genes without drug selection. In this model, spleen and lymph node (LN) B cells can be reproducibly infected within 40 hours with a retroviral vector containing the human ADA gene expressed from its own promoter. The target cells contain on average 1–3 copies of the provirus per cell, can express high levels of the human ADA protein, and when adoptively transferred into SCID hosts, can home properly to lymphoid organs and persist for at least 3 months without any detectable loss in the level of expression of the introduced gene.

Abbreviations used in the present invention are as follows: pro-promoter; enh-enhancer; PBS-primer binding site for DNA synthesis; PPT-polypurine track for DNA synthesis; E-encapsidation sequences for RNA packaging; attR+-a sequence that will form the right side of the attachment site relating to integration; attL+-the sequence that will form the left side of the attachment side relating to integration; attL+-the deletion of the original provirus left-side attachment site; and attR+-the deletion of the original right side attachment site.

The present invention allows one to select a eukaryotic gene of interest, insert the gene into a vector designed in accordance with the present invention, transfect a helper cell with the vector, harvest virus stock from the helper cell, use the harvested progeny virus to infect a target cell, and have the proviruses which are formed in the target cells express the inserted eukaryotic gene without expressing any retroviral proteins. Since there is no retroviral promoter that is active on the provirus, endogenous helper proteins cannot trigger production of a virus from the provirus. Since there is no retroviral promoter in the provirus, the provirus cannot provide a retrovirus signal that might trigger the host cell to act in an unintended way. The lack of retroviral promoter stops production of retroviral RNA.

The invention may be better understood by reference to the following Example, which is provided by way of exemplification and not limitation.

EXAMPLE 1

Efficient Gene Transfer into Lymphocytes

MATERIALS AND METHODS

Efficient Gene Transfer into Primary Murine Lymphocytes

Mice

Balb/cBy male and female mice were purchased from the Jackson Laboratory, Bar Harbor, Me.

Plasmids pN2 was a generous gift from E. Gilboa. pN2 and pAsADA are Moloney murine leukemia virus (MLV)-based retroviral vectors that contain the neomycin phosphotransferase II (neo) gene, which is expressed from the MLV long terminal repeat (LTR) promoter. pAsADA contains the human adenosine deaminase (ADA) gene, which is expressed from its endogenous promoter. This vector was kindly provided by Gene Therapy, Inc.

Virus-producing cell lines

The GP+E-86 cell line is an NIH 3T3-based, ecotropic murine packaging cell line (Markowitz et al., 1988, J. Virol. 62:1120). GP+E-86 cells were transfected with 5 /g of vector plasmid DNA using the polybrene/DMSO shock method (Kawai & Nishizawa, 1984, Mol. Cell Biol. 4:1172), followed by selection with G418 (0.35 mg/ml) and GPT (xanthine 0.25 mg/ml, mycophenolic acid 25 /g/ml, and hypoxanthine 15/g/ml). N2-transfected GP+E-86 cells yielded virus stocks of $2.0 \times 10^7$ colony-forming units (CFU) per ml, quantitated by inoculation of NIH 3T3 cells with serial dilutions of helper cell supernatant, followed by selection in the presence of G418 (0.35 mg/ml) for two weeks at which time colonies were counted. AsADA-transfected cells yielded virus stocks of $1.5 \times 10^7$ CFU/ml.

Preparation of double-negative (DN) thymocytes

Thymocytes from 3 to 5 week old mice were treated with a cocktail of the monoclonal antibodies GK1.5 (rat anti-mouse CD4) (Wilde et al., 1983, J. Immunol. 131:2178; Dialynas et al., 1983, J. Immunol 131:2445), 3.168 (rat anti-mouse CD8) (Sarmiento et al., 1980, J. Immunol. 125:2665) and a mixture of guinea pig and rabbit complement to remove CD4+ and CD8+ cells. This protocol routinely yields a DN cell population that contains less than 2% CD4+ and less than 0.5% CD8+ cells as analyzed by flow cytometry. DN cells are then cultured in RPMI media supplemented with gentamicin (50/g/ml) (GIBCO, Grand Island, N.Y.), 2-mercaptoethanol (50/M) (Sigma, St. Louis, Mo.), and stimulated with recombinant human interleukin-7 (rIL-7, 50 ng/ml) (PeproTech, Rocky Hill, N.J.) for 24 hours prior to infection.

Preparation of Peripheral Lymph Node Lymphocytes

Lymph nodes (LN) were obtained from adult mice. T lymphocytes were isolated by treatment of LN cell suspensions with the monoclonal antibody J11d, a rat anti-murine heat stable antigen (HSA) antibody, which removes practically all B cells from LN19 with the addition of complement. B lymphocytes were isolated by treatment of lymph node cell suspensions with the monoclonal antibody J1j, a rat anti-mouse Thy-1.2 antibody (Symington, 1981, J. Immunol. 127:2496) and complement. These procedures routinely yield enriched T and B cell populations which contain >97% T or B cells, respectively, as analyzed by flow cytometry. Fewer than 0.5% of B cells were detected in T cell-enriched populations, and similarly, fewer than 0.5% of T cells were detected in B cell-enriched populations (data not shown). T cells were then cultured in RPMI media supplemented with gentamicin (50/g/ml), 2-mercaptoethanol (50/M), and stimulated with concanavalin A (4/g/ml). After 24 hours, the cells were washed twice and resuspended in medium containing 10 ng/ml of recombinant murine interleukin-2 (PeproTech). B cells were stimulated with lipopolysaccharide (50/g/ml).

Virus infections

Gene transfer into primary lymphoid cells was attempted by co-cultivation with virus-producing cells, and by inoculation with supernatant from virus-producing cells. Infection by co-cultivation was carried out by plating $10 \times 10^6$ stimulated lymphoid targets at a density of $1 \times 10^6$ cells/ml RPMI media, onto a confluent lawn of irradiated (1600 rads) virus-producing cells in 100 mm tissue culture plates. Polybrene (6/g/ml) and rIL-7 (50 ng/ml) for DN thymocytes, rIL-2 (10 ng/ml) for T lymphocytes, or lipopolysaccharide (50/g/ml) for B lymphocytes was added to the media. Twenty-four hours later, primary target cells were harvested and cultured in fresh media containing stimulatory lymphokines/mitogens. 72 hours later, target cell genomic DNA was extracted for Southern blotting analysis, and protein extracts were made for assaying for ADA activity. Infection by inoculation was carried out by incubating $20 \times 10^6$ DN thymocytes in 5.0 ml of virus supernatant in the presence of rIL-7 (50 ng/ml) and polybrene (8/g/ml) for 2 hours at 37° C. Cells were centrifuged, resuspended in fresh media plus rIL-7 (50 ng/ml), and cultivated in tissue culture plates until harvesting. To ensure that the vector viral supernatants used to inoculate primary lymphocytes contained infectious vector virions, NIH 3T3 cells were typically infected in parallel to ensure that infectious vector virus was contained in the supernatant, and always observed infection of NIH 3T3 cells.

DNA Isolation and Southern Blot Analysis

Southern blotting with 10/g/lane of Sac I-digested genomic DNA was performed according to standard methods (Sambrook et al., 1989, Cold Spring Harbor Laboratory Press), using a 32P-labeled neo-specific probe, the 1.3 Kb Eco RI-Xho I fragment from pN2. The probe was labeled by random priming. Controls for copy number were made by digesting pN2 and pAsADA with Sac I, and loading amounts corresponding to 1 and 10 proviral copies/genome on the gel.

ADA Assay $1 \times 10^6$ target cells were lysed 2 days post-infection by freeze/thaw method, and the lysate was applied to a cellulose acetate plate (Helena Laboratories, Beaumont, Tex.). Human and murine ADA isoenzymes were separated by electrophoresis on cellulose acetate plates (Lim et al., 1989, Proc. Natl. Acad. Sci. USA 86:8892). Enzyme activity was detected by reaction of the separated ADA isoenzymes on the plate with an agar overlay containing adenosine (2 mg/ml) (Sigma), nucleoside phosphorylase (15/g/ml) (Boehringer Mannheim, Indianapolis, Ind.), xanthine oxidase (0.06 U/ml) (Boehringer Mannheim), phenazine methosulfate (0.01 mg/ml) (Sigma), and dimethylthiazol diphenyltetrazolium bromide (0.1 mg/ml) (Sigma) in phosphate buffer at 37° C. for 20 minutes in the dark.

FIG. 1 illustrates schematically the retroviral vectors of the present invention. N2 and AsADA are Moloney murine leukemia virus-based vectors. N213 contains the neomycin phosphotransferase II gene (neo), expressed from the viral long terminal repeat (LTR) promoter. AsADA contains neo, expressed from the viral LTR promoter, and the human adenosine deaminase gene (ADA), expressed from its endogenous promoter (As).

Figure 2A:
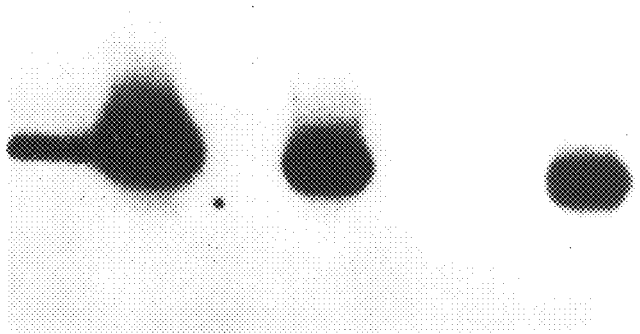
FIG. 2(A) and FIG. 2(B) are Southern blots showing gene transfer and expression in DN thymocytes.
Figure 2B:
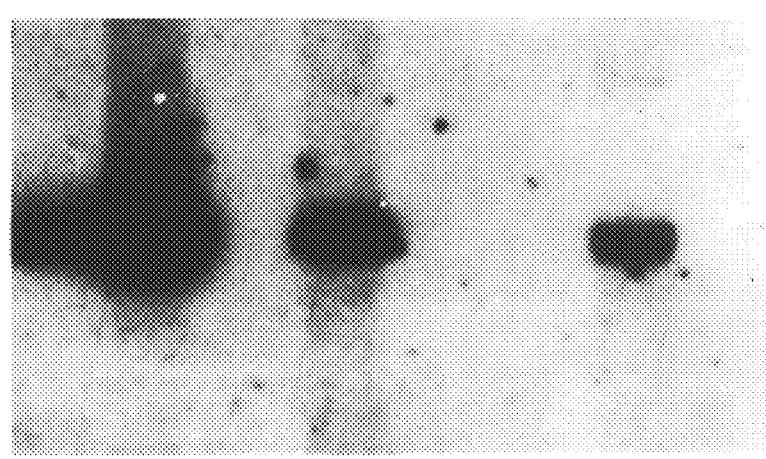

FIG. 2(A) and FIG. 2(B) are Southern blots showing gene transfer and expression in DN thymocytes. FIG. 2(A) is a Southern blot of N2-infected cells and FIG. 2(B) is a Southern blot of AsADA-infected cells. Genomic DNA was extracted two days post-infection, digested with Sac I, followed by Southern blotting using a neo-specific probe. 10/g of DNA was loaded in each lane. Lanes in FIG. 2(A) and FIG. 2(B): plasmid copy number controls corresponding to 1 (lane 1) or 10 (lane 2) proviruses/cell; untransfected GP+E-86 cells (lane 3); N2-(A, lane 4) or AsADA-(B, lane 4) producing GP+E-86 cells; uninfected DN thymocytes (lane 5); DN thymocytes infected in the presence of rIL-7 by inoculation with virus-containing producer cell supernatants for 2 hours (lane 6), or by co-cultivation on a confluent lawn of irradiated producer cells for 24 hours (lane 7); "lifting" control: supernatant from irradiated producer cells, plated as for co-cultivation, mixed with freshly obtained DN thymocytes immediately prior to genomic DNA isolation (lane 8).

Figure 2C:
FIG. 2(C) shows human ADA gene expression in murine DN thymocytes infected with AsADA.

FIG. 2(C) shows human ADA gene expression in murine DN thymocytes infected with AsADA. 48 hours after infection, target cell lysates (corresponding to $1 \times 10^5$ cells/lane) were electrophoresed on a cellulose acetate plate to separate the human from the murine ADA isoenzymes. ADA protein was detected by colorimetric enzyme assay. Lanes: uninfected DN thymocytes (lane 1); DN thymocytes inoculated with AsADA viral stocks (lane 2); DN thymocytes co-cultivated with AsADA-virus producing cells (lane 3); "lifting" control (lane 4); human standard: H9 cells (diluted 1:2, lane 5), human T cell line; AsADA-producer cells (diluted 1:10, lane 6).

FIG. 3 shows gene transfer and expression in lymph node T cells. T lymphocytes were isolated by treatment of lymph node cells with monoclonal antibody specific for J11d in the presence of complement. T cells were stimulated to divide by culture overnight with concanavalin A, followed by the addition of interleukin-2 during co-cultivation with irradiated AsADA-producing cells.

Figure 3A:
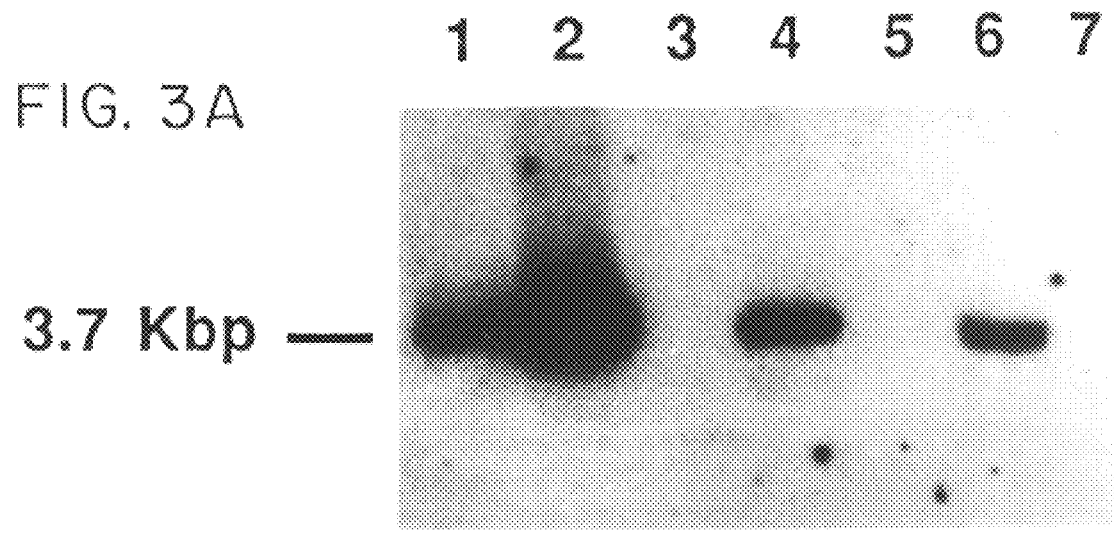
In FIG. 3(A), genomic DNA was extracted 48 hours after infection, followed by Southern blotting as described in the legend to FIG. 2.

In FIG. 3(A), genomic DNA was extracted 48 hours after infection, followed by Southern blotting as described in the legend to FIG. 2. Lanes: plasmid copy number controls equivalent to 1 (lane 1) and 10 (lane 2) proviral copies per cell; untransfected GP+E-86 cells (lane 3); AsADA-transfected GP+E-86 cells (lane 4); uninfected lymph node T lymphocytes (lane 5); lymph node T cells co-cultivated with AsADA-virus producing cells (lane 6); "lifting control" supernatant from irradiated AsADA-virus producing cells mixed with freshly obtained lymph node T lymphocytes just prior to DNA extraction (lane 7).

Figure 3B:
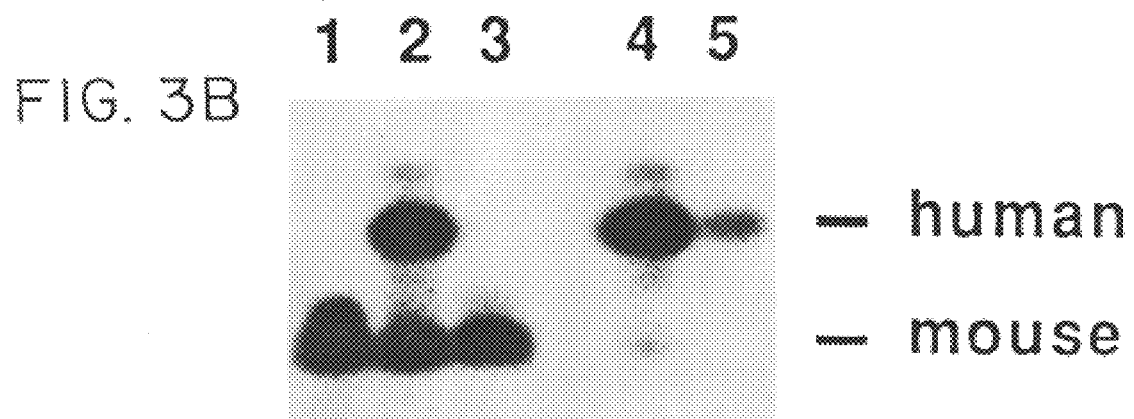
FIG. 3(B) shows human ADA gene expression in murine lymph node T lymphocytes infected with AsADA.

FIG. 3(B) shows human ADA gene expression in murine lymph node T lymphocytes infected with AsADA. 48 hours after infection, ADA assays were performed as described in the legend to FIG. 2. Lanes: "lifting" control (lane 1); lymph node T cells co-cultivated with AsADA-virus producing cells (lane 2); uninfected lymph node T cells (lane 3); AsADA-producer cells (diluted 1:10, lane 4); human standard: H9 cells (diluted 1:2, lane 5).

FIG. 4 shows gene transfer and expression in lymph node B cells. B lymphocytes were enriched for by culture of lymph node cells with monoclonal antibody specific for the pan-T cell marker Thy-1.2 in the presence of complement. B cells were stimulated to divide by culture with lipopolysaccharide one day prior to infection and during infection.

Figure 4A:
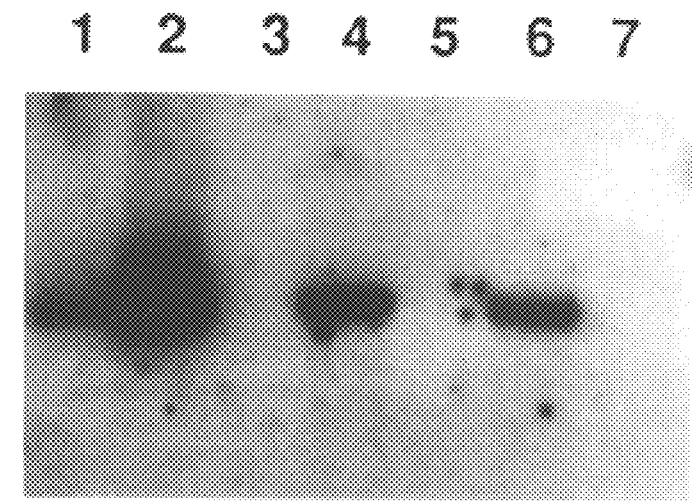
In FIG. 4(A), genomic DNA was extracted 48 hours after infection, followed by Southern blotting, as described in the legend to FIG. 2.

In FIG. 4(A), genomic DNA was extracted 48 hours after infection, followed by Southern blotting, as described in the legend to FIG. 2. Lanes: plasmid copy number controls corresponding to 1 (lane 1) and 10 (lane 2) proviral copies/cell; untransfected GP+E-86 cells (lane 3); AsADA-transfected GP+E-86 cells (lane 4); uninfected lymph node B cells (lane 5); lymph node B cells co-cultivated with AsADA-virus producing cells (lane 6); "lifting control" supernatant from irradiated AsADA-virus producing cells mixed with freshly obtained lymph node B cells immediately prior to DNA extraction (lane 7).

Figure 4B:
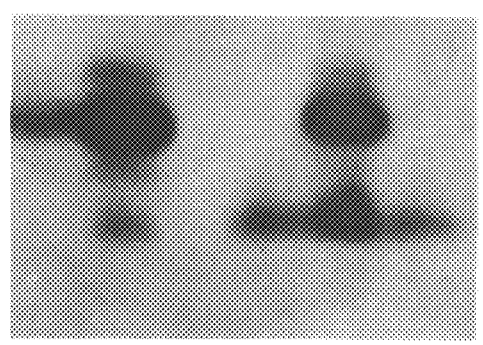
FIG. 4(B) shows human ADA gene expression in murine lymph node B lymphocytes infected with AsADA.

FIG. 4(B) shows human ADA gene expression in murine lymph node B lymphocytes infected with AsADA. 48 hours after infection, ADA assay was performed, as described in the legend to FIG. 2. Lanes: human standard: H9 cells (diluted 1:2. lane 1); AsADA-producer cells (diluted 1:10, lane 2); uninfected lymph node B cells (lane 3); lymph node B cells co-cultivated with AsADA-producer cells (lane 4); "lifting" control (lane 5). of vector genome copies in these cells.

Murine Model for B Cell Lineage Somatic Cell Gene Therapy

The murine leukemia virus (MLV)-based retroviral vector AsADA was used, containing the human ADA and the bacterial neomycin resistance (neo) genes (FIG. 4A), produced by the ecotropic packaging cell line GP+E-86 (Braakman et al., 1992, Eur. J. Immunol. 22:63). Enriched populations of B lymphocytes were obtained by depletion of T cells from adult C.B-17 spleen or lymph nodes. To facilitate efficient proviral integration, B cells were induced to proliferate with the mitogen lipopolysaccharide (LPS) for 16 hours, and then co-cultivated with lethally-irradiated helper cells for 24 hours. With this method, an infection efficiency of 1 to 3 proviral copies per target cell genome for both splenic and LN B cells was routinely obtained (FIG. 4B, lanes 4 and 5). This was assessed by Southern blotting of target cell genomic DNA 40 hours after infection, using a probe specific for neo sequences present in the provirug, and compared to AsADA plasmid copy number controls equivalent to 5, 1 or 0.5 proviruses/genome (FIG. 4B, lanes 1–3). FIG. 4B, lane 6 represents a control designed to rule out the possibility that part of the observed signal is due to contaminating helper cells that may have lifted during co-cultivation. No signal was detected in this control.

Human ADA protein expression was assayed in parallel employing a colorimetric enzymatic assay using target cell lysate that had been electrophoresed to separate the exogenous human ADA from the endogenous murine ADA enzyme (Hayden & Ma, 1992, Mol. Cell. Biochem. 113:171; Auwerx et al., 1992. Critical Reviews in Clinical Laboratory Sciences). As can be seen in FIG. 4C, lanes 3 and 4, the human ADA enzyme activity in both splenic and LN B cells was higher than the murine ADA activity. No signal resulting from potentially lifted helper cells was detected (FIG. 4C, lane 5).

Since Southern blotting indicated that the infection protocol could be completed within 40 hours, yielding very efficient gene transfer without the need for an in vitro drug selection step to enrich for infected cells, it was postulated that the primary B cells would retain their viability and normal homing patterns in vivo. To test this, the homing patterns of C.B-17 spleen B cells infected with the AsADA retroviral vector were compared to that of fresh spleen B cells. $^{51}$Cr-labeled B cells were transferred i.v into groups of 3 Igh-congenic Balb/cBy SCID mice. Recipients were sacrificed 18 hours later and various organs were removed and levels of radioactivity were measured. As shown in Table 1, AsADA- infected spleen B cells exhibited homing patterns similar to fresh spleen B cells. In both groups, cells homed mainly to the spleen of recipient mice, as is consistent with published reports (Sprent, 1973, Cell. Immunol. 7:10; Stevens et al., 1982, J. Immunol. 128:844), although the percentage of infected cells that reached the spleen, 7.14%, was reduced compared to that of the control cells, 13.16%. Levels of radioactivity were highest in the liver in both groups, since the liver clears damaged lymphocytes. The ratio of counts in the spleen compared to the liver is a measure of the viability of the transferred cells. For infected cells, the spleen to liver ratio was 0.28, vs. 0.65 for freshly obtained B cells (anti-Thy-1.2 plus complement treatment only), indicating that the 40 hour co-cultivation protocol reduced the number of viable cells that home to the spleen by approximately half.

TABLE 1

Homing pattern of $^{51}$Cr-labeled AsADA-infected spleen B cells injected i.v into SCID mice. C.B-17 spleen B cells (anti- Thy-1.2+complement-treated) were stimulated with LPS for 18 hours then co-cultivated with AsADA producer cells as described in FIG. 4 for 24 hours, prior to labeling with $^{51}$Cr. Freshly obtained splenic B cells (control) were simultaneously labeled. 5×10$^6$ labeled cells were injected into 3 mice for each group. 18 hours after injection recipients were killed and radioactivity from various organs was measured in a gamma-counter.

|  | Percent of Injected Radioactivity* | |
|---|---|---|
| Radioactivity | Control | AsADA-infected |
| spleen | 13.16 (0.6) | 7.14 (0.6) |
| liver | 20.23 (0.6) | 25.55 (<0.1) |
| gut | 2.02 (0.5) | 1.06 (0.7) |
| legs (BM) | 4.43 (0.6) | 1.85 (0.6) |
| lungs | 2.03 (0.6) | 2.15 (0.6) |

*Mean of data (SD) from 3 mice/group

To assess whether AsADA-infected B cells persist long-term in vivo, both splenic and LN B cells from C.B-17 mice were infected with the AsADA vector virus as described, then adoptively transferred to 10 Igh-congenic Balb/cBy SCID mice (5–25×10$^6$ cells/mouse i.v).

Figure 5A:
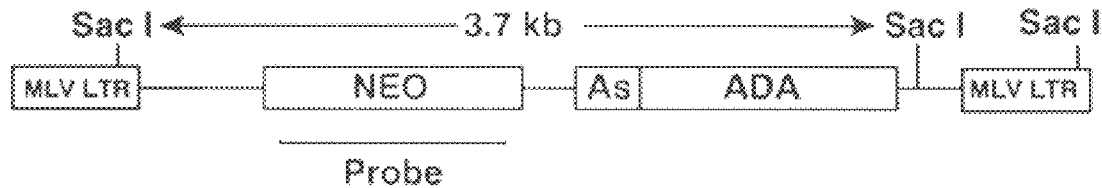
FIG. 5(A) illustrates schematically the retroviral vector AsADA. AsADA is a G1Na vector (Miller et al., 1992, Hum. Gene Ther. 3:619) containing the bacterial neo gene expressed from the MLV LTR promoter, and the human ADA gene expressed from its endogenous promoter.

FIG. 5(A) illustrates schematically the retroviral vector AsADA. AsADA is a GiNa vector (Miller et al., 1992, Hum. Gene Ther. 3:619) containing the bacterial neo gene expressed from the MLV LTR promoter, and the human ADA gene expressed from its endogenous promoter. Ecotropic GP+E-86 helper cells (Braakman et al., 1992, Eur. J. Immunol. 22:63) produce AsADA at a titer of 2×10$^7$ CFU/ml, as assayed by inoculation of NIH 3T3 cells with serial dilutions of helper cell supernatants. AsADA producer cells were regularly tested and always found to be negative for production of replication-competent virus, by assaying for reverse transcriptase activity in inoculated NIH 3T3 cells.

Figure 5B:
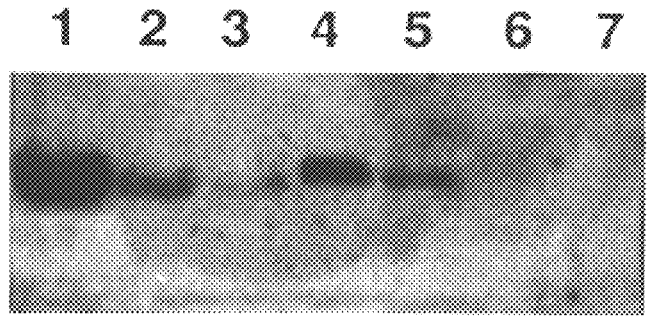
FIG. 5(B) is a Southern blot analysis of splenic and LN B cells infected with AsADA.

FIG. 5(B) is a Southern blot analysis of splenic and LN B cells infected with AsADA. Primary C.B-17 B cells were obtained by treating spleen or LN cells with the anti-Thy-1.2 mAb J1j and complement (Braakman et al., 1992, Eur. J. Immunol. 22:63). B cells were cultured overnight with LPS (50/g/ml), prior to infection with AsADA by co-cultivation on a confluent lawn of lethally-irradiated helper cells in the presence of LPS for 24 hours, as described previously (Kuo et al., Blood, in press). Genomic DNA was extracted from the target cells 48 hours later, and Southern blotting was performed using the restriction enzyme SacI, which yields a 3.7 kb proviral fragment after hybridization with a neo-specific sequence. Lanes: 1–3, SacI-digested pAsADA plasmid DNA equivalent to 5, 1 and 0.5 proviral copies/cell; 4, AsADA-infected splenic B cells; 5, AsADA- infected LN B cells; 6, a supernatant control to assay whether helper cell lifting during the co-cultivation contributed to the signal obtained from the target cells. Uninfected LN cells (used as a carrier for the small number of helper cells that may lift) were added to the supernatant from irradiated helper cells that had been plated as for co-cultivation immediately prior to genomic DNA extraction; 7, uninfected LN cells.

Figure 5C:
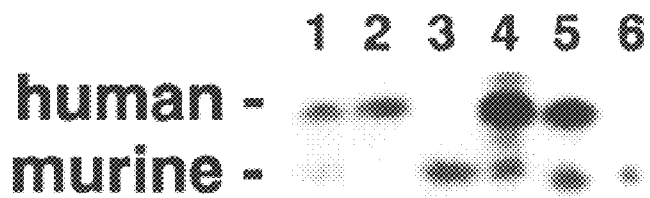
FIG. 5(C) shows a human ADA assay in murine B cells.
Figure 6A:
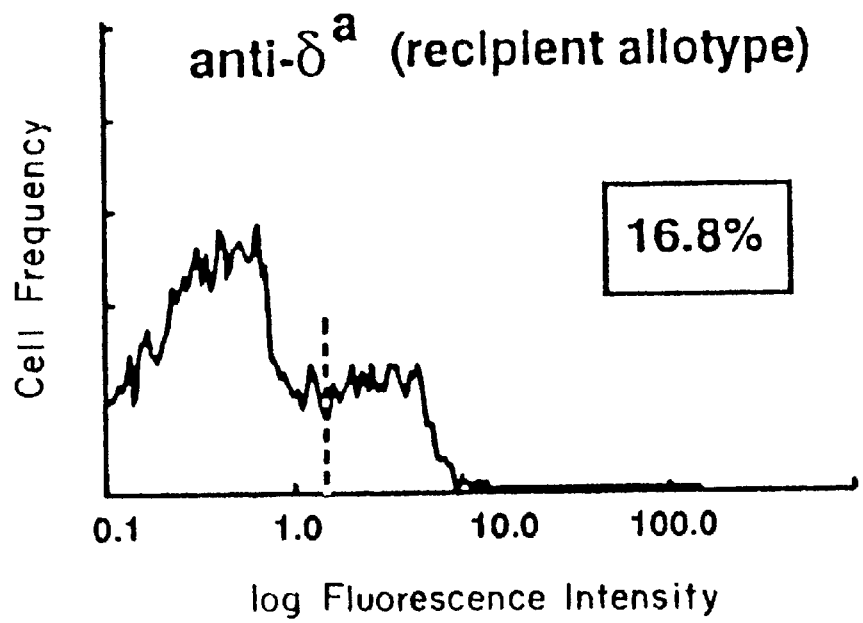
FIG. 6 shows a flow cytometric analysis of spleen from SCID mice reconstituted with AsADA-infected LN and spleen B cells. Spleen cells were analyzed by flow cytometry 4 weeks post-transfer from a representative mouse injected with LN B cells FIG. 6(A,B), and 3 months post-transfer from a mouse injected with splenic B cells FIG. 6(C,D).
Figure 6B:
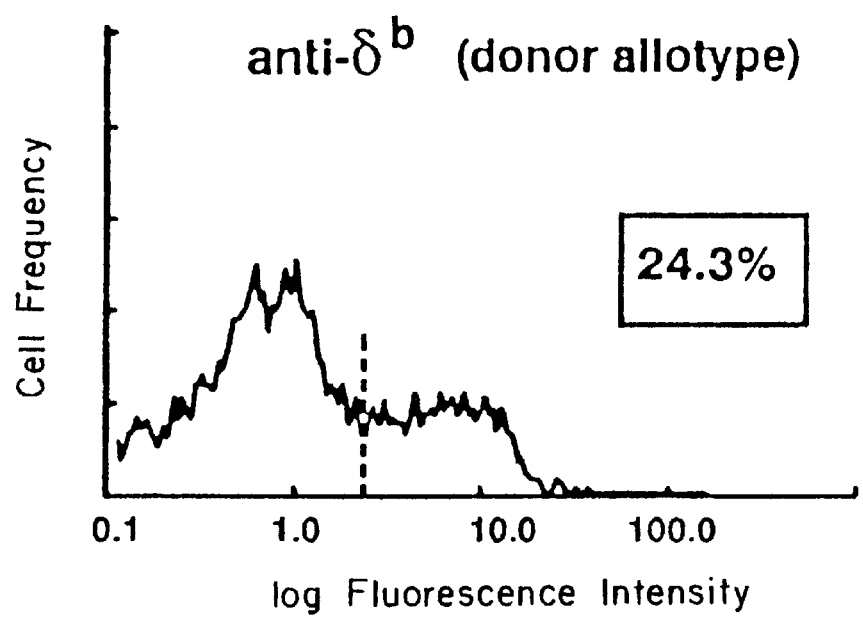
Figure 6C:
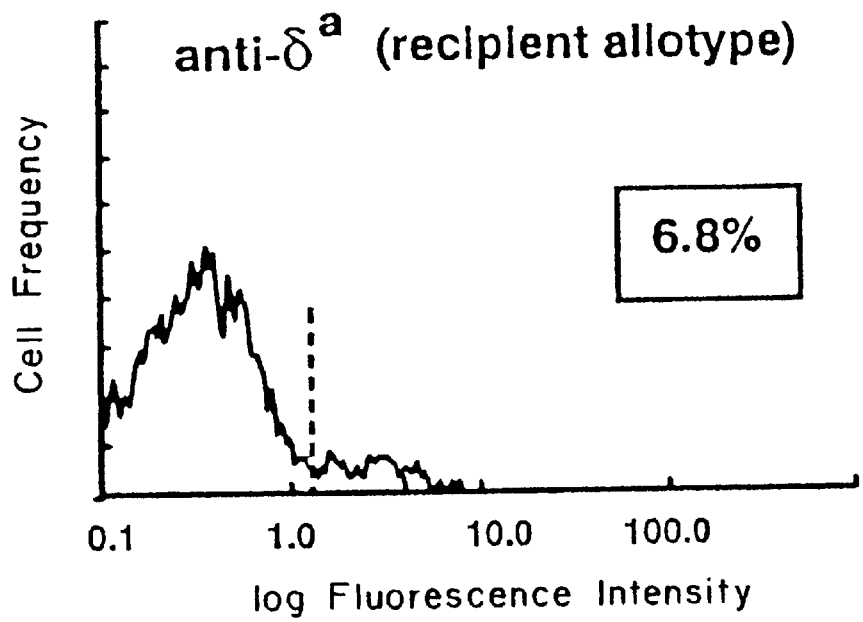
Figure 6D:
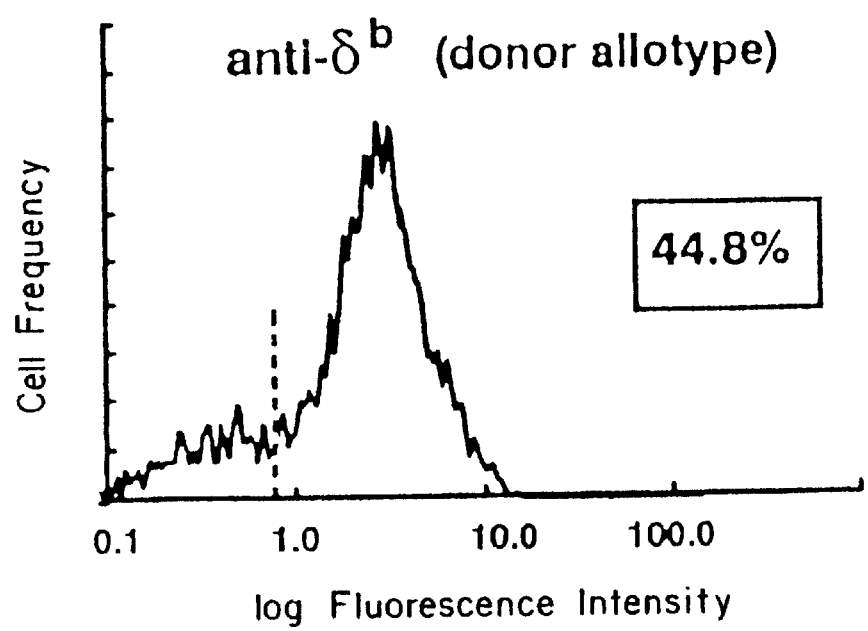

FIG. 5(C) shows a human ADA assay in murine B cells. In parallel experiments, 48 hours after infection, the lysate from 1×10$^6$ target cells was electrophoresed on a cellulose acetate plate to separate human from murine ADA enzymes, then ADA activity was detected by colorimetric enzyme assay (Kuo et al., Blood, in press). Lanes: 1, AsADA producer cells; 2, human standard: H-9 T cell line; 3, murine standard: uninfected LN cells; 4, splenic B cells infected with AsADA; 5, LN B cells infected with AsADA; 6, a supernatant control (as in B).

FIG. 6 shows a flow cytometric analysis of spleen from SCID mice reconstituted with AsADA-infected LN and spleen B cells. LN and splenic B cells from C.B-17 mice were infected with AsADA as described in the legend to FIG. 4B, and injected into lightly-irradiated (200 rad) Igh-congenic BALB/cBy SCID mice (5×10$^6$ LN B cells, 17×10$^6$ splenic B cells, i.v). Spleen cells were analyzed by flow cytometry 4 weeks post-transfer from a representative mouse injected with LN B cells FIG. 6(A,B), and 3 months post-transfer from a mouse injected with splenic B cells FIG. 6(C,D). 10$^6$ cells were stained with monoclonal antibodies specific for the donor C.B-17 Igh allotype $^b$, and the recipient BALB/cBy Igh allotype $^a$ (Oi et al., 1978, Curr. Top. Micro. Immunol. 81:115). 5000 cells were analyzed on an Epics Profile.

Figure 7A:
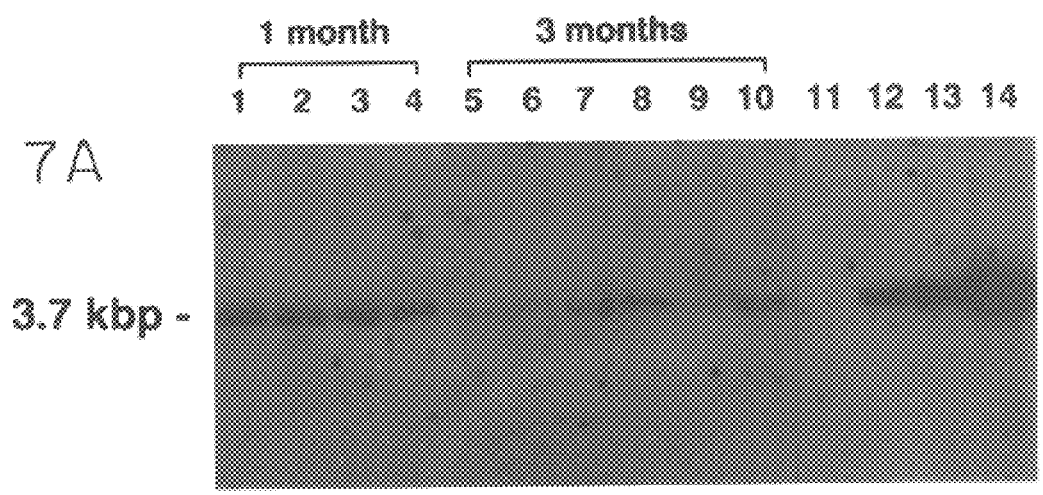
FIG. 7(A) shows a Southern blot analysis of genomic DNA from the spleen of SCID mice that were adoptively transferred with target B cells.

FIG. 7(A) shows a Southern blot analysis of genomic DNA from the spleen of SCID mice that were adoptively transferred with target B cells. Splenic B cells were infected with AsADA as described in FIG. 4B, and injected immediately into 10 SCID mice (5–25×10$^6$ cells/mouse i.v). Recipient mice were sacrificed 1 and 3 months later, and genomic DNA was extracted from the spleens. Southern blotting was performed as described in FIG. 4. Lanes: 1–4, recipient mice sacrificed 1 month post-transfer; or 5–10, 3 months post-transfer; 11, control spleen from an unreconstituted mouse; 12–14, SacI- digested pAsADA plasmid DNA equivalent to 0.5, 1, and 5 proviral copies/cell, respectively.

Figure 7B:
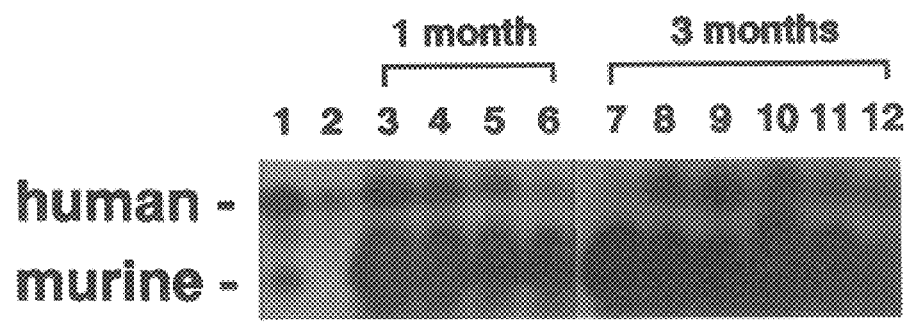
FIG. 7(B) shows the human ADA activity in SCID mice.

FIG. 7(B) shows the human ADA activity in SCID mice. Spleen cell lysates corresponding to 1×10$^6$ lymphocytes were assayed for human ADA activity as described in FIG. 4. Lanes: 1, AsADA helper cells; 2, human H-9 T cell line; 3–6, recipient spleens 1 month post-transfer; or 7–12, 3 months post-transfer.

Results

Efficient Gene Transfer into Primary Murine Lymphocytes

Efficient Gene Transfer into DN Thymocytes

CD4-CD8-(DN) thymocytes were derived from 3 to 5 week old mice, by incubation of thymocytes with anti-CD4 and anti-CD8 monoclonal antibodies in the presence of complement. For these studies the vectors N2 and AsADA were used. Both N2 and AsADA are Moloney murine leukemia virus (MLV)-based vectors. The ecotropic packaging cell line, GP+E-86,14 was used to produce virus. These cells have been designed to produce MLV-based vector virus in the absence of replication-competent MLV. N2 contains the neomycin phosphotransferase II gene (neo) and AsADA contains both the neo and human adenosine deaminase genes (ADA) (FIG. 1).

DN thymocytes were infected by co-cultivation with irradiated, confluent cultures of either N2- or AsADA-vector virus-producing cells or by inoculation with virus-containing, supernatants in the presence of recombinant human interleukin-7 (rIL-7).21 rIL-7 is required to stimulate the DN thymocytes to proliferate, a requisite step for infection by MLV-based vector virus (Richter et al., 1984, Mol. Cell Biol. 4:151). Twenty-four hours after co-cultivation, target cells were transferred to new plates and cultured for 2 days to allow any lifted producer cells to re-adhere. This incubation period also allows the cells time to express the transferred gene. Cells were then analyzed for integration of viral DNA by Southern blot analysis, and for the presence of the human ADA protein by enzymatic assay.

Genomic DNA was digested with Sac I. Successful provirus formation should yield a 3.3 kb band in N2-infected cells, and a 3.7 kb band in AsADA-infected cells after hybridization with a 1.3 kb neo-specific sequence (FIG. 1). As shown in FIG. 2, a signal equivalent to approximately 1 to 5 proviruses per cell (quantitated by scanning gel densitometry and compared to plasmid controls equivalent to 1 or 10 copies) was obtained after co-cultivation of DN thymocytes with irradiated N2 producer cells (FIG. 2A, lane 7) or AsADA producer cells (FIG. 2B, lane 7). In contrast, the cells infected by inoculation yielded very weak signals, N2-inoculated (FIG. 2A, lane 6), AsADA-inoculated (FIG. 2B, lane 6), which were only detectable after a 2 week exposure (data not shown). The signals corresponded to approximately 0.1 proviruses per cell, indicating that infection by inoculation is approximately 50 times less efficient than infection by co-cultivation. It should be noted that infection of primary lymphocytes was attempted by inoculation with longer incubation periods including 6 hours and overnight. Moreover, this was carried out with concentrated viral preparations in which the viral titers were increased approximately 8-fold ($1 \times 10^8$ titer per ml on NIH 3T3 cells). Even with concentrated virus stocks and longer incubation periods, efficient gene transfer was not obtained as with co-cultivation. Uninfected, control lymphocytes (FIG. 2A and B, lanes 5) and GP+E-86 cells (FIG. 2A and B, lanes 3) were negative for neo. N2-producer cells (FIG. 2A, lane 4) and AsADA-producer cells (FIG. 2B, lane 4) served as positive controls.

Although thymocytes infected by co-cultivation were added to fresh tissue culture plates to allow any producer cells that might have lifted during the co-cultivation procedure to re-adhere, it was believed that it was still useful to control for helper cells that might be contaminating the primary cell cultures even after this step. To control for this, supernatants from irradiated AsADA- and N2-helper cells cultured without lymphocytes were assayed. They were subjected to the same manipulations as cultures co-cultivated with lymphocytes. These supernatants were then added to freshly obtained DN thymocytes followed immediately by extraction of genomic DNA (an aliquot of the AsADA supernatant mixture was saved for later use in the ADA assay). DN thymocytes were added to act as carrier cells since the number of lifted cells might have been small relative to the number. As can be seen in FIG. 2 (A and B, lanes 8) no signals were obtained from this control, indicating that the positive signals from infected double negative thymocytes (FIG. 2A and B, lanes 7) were not due to contaminating helper cells.

Expression of the Human ADA Gene in Murine DN Thymocytes

DN thymocytes infected with the retroviral vector AsADA either by co-cultivation or by inoculation as described in the previous section, were harvested, transferred to new plates and incubated for 2 days to allow sufficient expression of the human ADA gene, and in the case of the co-cultivated target cells, to also allow any lifted helper cells to re-adhere. The target DN thymocytes were then assayed for human ADA protein expression. FIG. 2C depicts an ADA assay of the target DN thymocytes. The human ADA protein was separated from the murine ADA isoenzyme by electrophoresis of target cell lysate on cellulose acetate plates. Detection of the protein is by colorimetric enzyme assay (Material and Methods). The results show that the exogenous human ADA gene was expressed in the co-cultivated thymocytes. The level of expression was somewhat lower than expression of the endogenous murine ADA gene (FIG. 2C, lane 3). No expression of human ADA was seen in the DN thymocytes inoculated with free AsADA-vector virus stocks (FIG. 2C, lane 2). This result is in concurrence with the extremely low provirus copy number obtained by inoculation of DN thymocytes (FIG. 2B, lane 6). Murine DN thymocytes and human H-9 cells (T cell line) were used as standards for the murine and human isoenzymes (FIG. 2C, lanes 1 and 5, respectively). FIG. 2C, lane 4 represents a "lifting" control, using supernatant from irradiated AsADA-helper cells that were not co-cultivated with thymocytes, mixed with freshly obtained DN thymocytes immediately prior to ADA assay. Human ADA expression was not detected, indicating that the ADA signal obtained from the co-cultivated DN thymocytes is not due to helper cell contamination.

Efficient Transfer and Expression of the Human ADA Gene in Murine Lymph Node T and B Lymphocytes Lymph node T and B cells were prepared as described in the Material and Methods. Cells were stimulated for 24 hours with either Con A for T cells or LPS for B cells, then washed and co-cultivated on a confluent irradiated lawn of AsADA-producer cells in the presence of polybrene, and rIL-2 (T cells) or LPS (B cells). After 24 hours the target cells were transferred to fresh plates and cultured for 48 hours, to allow any lifted helper cells to re-adhere. Cells were then harvested and genomic DNA was extracted, or aliquots were taken for ADA assay of protein expression.

Southern blotting of target cell DNA demonstrated that an average of approximately one vector provirus per cell could be transferred to both T and B lymphocytes (FIG. 3A and 4A, lanes 6) when compared to plasmid copy number controls equivalent to 1 and 10 copies per cell (FIG. 3A and 4A, lanes 1 and 2, respectively). A "lifting" control, performed by mixing the supernatant from irradiated plates of helper cells that were not co-cultivated with target cells with freshly obtained lymph node cells immediately prior to DNA extraction or ADA assay, yielded no signal (FIG. 3A and 4A, lanes 7). Again this indicates that the signals obtained from the co-cultivated target cells were not due to contamination from lifted helper cells.

ADA assay of target cell lysates showed that both lymph node T and B lymphocytes co-cultivated with AsADA-producer cells expressed the exogenous human ADA protein at levels comparable to the endogenous murine isoenzyme (FIG. 3B, lane 2; FIG. 4B, lane 4). The "lifting" control, as described previously, for contaminating helper cells, did not yield an ADA signal (FIG. 3B, lane 1; FIG. 4B, lane 5). These results suggest that the efficiency of infection is high, approximately one copy per cell, and the level of expression of the exogenous ADA gene is comparable to the level of expression of the endogenous gene.

Murine Model for B Cell Lineage Somatic Cell Gene Therapy

As depicted in FIG. 6, the infected B cells homed mainly to the spleen of the recipient mice, where they were detected for at least 3 months by flow cytometric (FACS) analysis using monoclonal antibodies specific for the donor type Igh-5 (/) allotypic marker (Oi et al., 1978, Curr. Top. Micro. Immunol. 81:115). Splenic B cells were better able to reconstitute the B cell compartment of the recipient mice than LN B cells, however, donor type LN B cells were also readily detected in SCID spleen. FIG. 6A,B depicts flow cytometric analysis of the spleen of a representative SCID mouse adoptively transferred with LN B cells. 24.3% of the lymphocytes in the spleen expressed the donor Igh-5 allotype and 16.8% expressed the host Igh-5 allotype. The host type cells are most probably "leaky" cells that are found in most C.B-17 SCID mice (Bosma et al., 1988, J. Exp. Med. 167:1016). FIG. 6C,D depicts flow cytometric analysis of the spleen of a representative SCID mouse adoptively transferred with splenic B cells. 44.8% of the lymphocytes were of donor origin, and only 6.8% were of host origin 3 months post- transfer. Donor-type lymphocytes were also detected in LN, however, in small numbers (data not shown). This is consistent with published reports that B cells home preferentially to the spleen after adoptive transfer into mice (Oi et al., 1978, Curr. Top. Micro. Immunol. 81:115). Also, since LN in SCID mice atrophy, it may take a long time for the LN to reach normal size following reconstitution of the lymphoid system. It is probable that a much larger influx of lymphocytes is required for full LN reconstitution than was performed with the cell transfer. Persistence of infected cells and exogenous gene expression were detected for at least 3 months in the spleen and lymph node of recipient animals. Southern blotting of total genomic DNA isolated from whole spleen at 1 month and 3 months post-transfer was positive for proviral sequences in all 10 mice tested, without the need for PCR amplification to detect the signal. In FIG. 7A, lanes 1–10, the proviral signals are shown for the 10 mice at 1 and 3 months after adoptive transfer. Compared to AsADA plasmid copy number controls equivalent to 0.5, 1, and 5 proviruses/cell (FIG. 7A, lanes 12–14, respectively), the provirus is present in each spleen ranging between 0.1 to 0.5 copy/cell, depending on the number of non-lymphoid and leaky cells also present in each spleen. It is important to note that only a small percentage of the cells in the spleens of the reconstituted SCID mice are lymphocytes and therefore most of the DNA analyzed is derived from irrelevant, non-lymphoid cells. These results therefore corroborate the data in FIG. 4, providing conclusive evidence that the efficiency of gene transfer was very high, and that the infected cells (or their progeny) persist in significant numbers for at least 3 months. Genomic DNA extracted from kidney and liver from some of the mice, was always found to be negative for proviral sequences (data not shown).

DISCUSSION

Efficient Gene Transfer into Primary Murine Lymphocytes

The ability to introduce a gene into primary lymphocytes during a relatively short period of time in vitro is particularly important, since it minimizes cell damage and cell surface alterations which usually result in inappropriate homing in vivo. There have been previous reports of retroviral-mediated gene transfer into T cells. However, these reports have been mostly limited to transformed T cell lines (Krauss et al., 1991, Human Gene Therapy 2:221), long-term T cell clones (Culver et al., 1991, Proc. Natl. Acad. Sci. USA; Uchida et al., 1986, J. Immunol 136:1876), or tumor infiltrating lymphocytes (TIL) obtained after long-term expansion in the presence of IL-2 (Culver et al., 1991, Proc. Natl. Acad. Sci. USA 88:3155), and in the majority of instances drug selection was required to enrich for the infected population. The one report depicting gene transfer into primary T cells within a few days after explantation described on average gene transfer into only 5% of the primary T cells, and this was only determined for the cytotoxic T lymphocyte sub-population (Reimann et al., 1986, J. Immunol. Methods 89:93). Thus, besides describing for the first time efficient gene transfer into primary B cells and DN thymocytes, this invention describes the first delineating efficient gene transfer into primary mature T cells, which have not been expanded for long periods in vitro.

The data described herein show that gene transfer approached on average 1 to 5 proviruses per cell and that the level of expression of the exogenous ADA gene was comparable to that of the endogenous ADA gene in the target cell population. Although it is not certain from the experiments described that every cell has been targeted, it seems likely that a large percentage of the cells have been infected. If for example only 1% of the cells were effectively infected, they would harbor 100 to 500 proviruses per cell which would result in a heavy mutational burden and in all likelihood have deleterious effects upon their normal functioning and survival. Homing experiments using SCID mice as recipients indicated that the infected cells retain their ability to home properly and expression of the human ADA gene could be detected for at least two months in these animals post-transfer (manuscript in preparation). Thus, it seems unlikely that only a small percentage of the cells have been targeted. However, to more accurately assess the proportion of infected cells, vectors encoding histochemically detectable proteins (such as β-galactosidase and the human placental alkaline phosphatase) (Fields-Berry et al., 1992, Proc. Nati. Acad. Sci. USA 89:693) are being constructed for future studies.

There were a few parameters which seem to be important for efficient gene transfer into primary murine lymphocytes: 1) the producer cell lines needed to produce virus stocks yielding a titer of about $10^7$ CFU/ml on NIH 3T3 cells. It should be noted that gene transfer into primary DN thymocytes was examined using different helper cell clones which produced vector virus titers ranging from $1\times10^6$ to $2\times10^7$ per ml on NIH 3T3 cells. Gene transfer into the primary cells using co-cultivation began to approach one provirus per cell only when the corresponding titers on NIH 3T3 cells neared $10^7$/ml. Thus, once this was observed, gene transfer into primary cells was only attempted with producer cells yielding titers in the range of $10^7$/ml; 2) co-cultivation with lethally irradiated virus-producing cells, as shown for other protocols (Culver et al., 1991, Proc. Natl. Acad. Sci. USA 88:3155; Van Beusechem et al., 1992, Proc. Natl. Acad Sci USA 89:7640), was much more efficient than infection with free virus stocks. Supernatant inoculation versus co-cultivation for transfer into mature T and B cells was also tested. As with DN thymocytes, supernatant inoculation was not nearly as efficient as co-cultivation for efficient gene transfer (data not shown). 3) As expected the presence or the absence of the appropriate mitogen and/or growth factor is important for efficient gene transfer since the retroviral vectors used are derived from the MoMLV oncoretrovirus, which requires cellular replication for provirus formation (Richter et al., 1984, Mol. Cell Biol. 4:151).

With the AsADA vector good expression of the introduced human ADA gene in the primary cell targets was obtained, comparable to the expression levels of the endogenous ADA gene. However, similar levels of expression with other vectors were not obtained. A number of different murine leukemia virus-based vectors were used utilizing various promoters, with inconsistent expression results in primary cells, (even though consistently good efficiency of transfer was obtained with all vectors used employing the co-cultivation protocol). The other promoters utilized include the herpes simplex virus tk promoter, the SV40 early gene promoter, and the cytomegalovirus immediate early gene promoter. However, it should be noted that these promoter might yield acceptable levels of expression in primary lymphocytes in a different vector context. It was found that almost all of the vectors express well in various established cell lines such as NIH 3T3 and BW5417. However, the ability of the vector to express in immortalized or tumor cell lines was a poor indication of its ability to express in primary lymphocytes.

There are a number of diseases which might be amenable to treatment by gene transfer into primary lymphocytes. Already, primary human lymphocytes from patients with severe combined immunodeficiency (SCID) caused by a defect in the adenosine deaminase (ADA) gene, have been used as recipients for retroviral-mediated transfer of the normal human ADA gene (Culver et al., 1991, Human Gene Therapy). One important factor for selecting this SCID disease for the first treatment employing somatic cell gene therapy was that transfer of the normal ADA gene would confer a selective growth advantage to the patient's lymphocytes that were successfully infected and expressed the exogenous ADA gene. Consequently, one could expect to obtain therapeutic benefit without the need for very efficient gene transfer approaching one exogenous gene per cell. However, more efficient gene transfer into primary B and T cells could enhance treatment even of this disease. These experiments demonstrate efficient gene transfer into primary LN B and T cells are a relevant model for efficient gene transfer into peripheral blood lymphocytes since lymph nodes and peripheral blood contain very similar ratios of T and B cell subsets. The reason LN T and B cells were used is that it is much easier to obtain the numbers of cells required to perform the experiments described from the lymph nodes of mice instead of from their peripheral blood.

For other diseases the importance of efficiently introducing exogenous genes into primary lymphocytes is more crucial. For example, intracellular immunization protocols have been proposed for treatment of patients infected with HIV (Baltimore, 1988, Nature 335:395). These protocols would involve efficient transfer of HIV cis-acting sequences to compete for the binding of HIV immunoregulatory proteins (Zimmerman, et al., 1992, Human Gene Therapy 3:155), and/or genes encoding trans-dominant mutant HIV regulatory proteins to inhibit HIV replication (Pearson et al., 1990, Proc. Natl. Acad. Sci. USA 87:5079; Malim et al., 1989, Cell 58:205; Hope et al., 1992, J. Virol 66:1849). Recently, Malim et al. (Malim et al., 1989, Cell 58:205) reported that T cell lines transduced with a retroviral vector encoding a trans-dominant mutant of the HIV rev protein failed to support HIV replication. This result suggests that efficient transduction of trans-dominant mutant genes into peripheral CD4+ T cells or lymphoid stem cells has potential therapeutic importance with respect to AIDS.

Adoptive immunotherapy (Howes et al., 1979, Nature 277:67; Byrne & Oldstone, 1984, J. Virol. 51:682; Greenberg, 1991, Adv. Immunol 49:281) is another procedure that can benefit from efficient gene transfer into primary lymphocytes. Recently, a number of procedures have been proposed which involve the in vitro expansion of autologous T cells for transplantation into patients to assist in combating cancer (Greenberg, 1991, Adv. Immunol. 49:281), infections in immunocompromised hosts (Riddell et al., 1992, Science 257:238), and AIDS (Miller, 1992, Nature 357:455). Genetic manipulation of these cells might offer added advantages in providing more potent responses and additional levels of safety. The types of genes that are potentially useful for this purpose include those encoding immunoregulatory molecules capable of augmenting immune responses, or growth stimulators that can induce autocrine expansion of the lymphocytes after reintroduction into a patient. This could eliminate the need for long-term cell expansion in vitro, which is currently required in order to accumulate enough cells of therapeutic benefit (Riddell et al., 1992, Science 257:238; Miller, 1992, Nature 357:455). Also of potential importance is the efficient introduction of "suicide" genes (Lupton et al., 1991, Mol. Cell Biol. 11:3374) that can be used to destroy the transplanted cells, in the event that they become tumorigenic, develop any other abnormalities, or are no longer necessary.

In addition to its predicted value for somatic cell gene therapy, genetic manipulation of primary lymphocytes might prove useful for studying basic questions in lymphocyte biology. For example, efficient transfer of immunoregulatory genes into immature DN thymocytes and other lymphocyte precursors is potentially important for studies of T cell development. Also, gene marking of progenitor lymphoid cells with retroviral vectors offers a tool for the study of lymphocyte differentiation and homing.

In summary, it was demonstrated that retroviral vectors can be used to efficiently introduce exogenous genes into primary murine lymphocytes, on an average of one to five copies per cell without the need for drug selection to enrich for stably infected cells. Moreover, it was shown that the transferred human ADA gene is expressed at high levels in these cells, particularly in mature T and B cells. This indicates that the murine system represents a suitable model for gene therapy requiring efficient gene transfer into primary cells of the lymphoid lineage.

Murine Model for B Cell Lineage Somatic Cell Gene Therapy

Exogenous gene expression was demonstrated in all of the recipient mice both at 1 month and 3 months post-transfer, by enzymatic assay for human ADA activity in cell lysates made from whole spleen tissue. FIG. 7B, lanes 3–12 depict human ADA activity in the mice represented in FIG. 7A. In SCID spleen, the human ADA activity does not appear as strong as the murine ADA activity due to the fact that there are many other types of cells present in the spleen which express the endogenous ADA gene (cells of the myeloid lineage and erythrocytes). When this is taken into account, the level of expression of the exogenous gene correlated well with the percentage of donor lymphocytes in each mouse, quantitated by FACS analysis as in FIG. 6 (data not shown). As is evidenced in FIG. 7B, the level of expression of human ADA did not decrease over time between 1 month and 3 months, and in fact remained level at 6 months and 9 months, post-transfer. Although it appears that the level of human ADA in each mouse does not precisely correlate with the proviral copy number, this is misleading, since the results reflect differences inherent in the assay procedures. The ADA assay is performed on a volume of spleen tissue from each mouse that corresponds to $1 \times 10^6$ counted lymphocytes. Host cells do not dilute out the signal for exogenous human ADA, but instead contribute to the larger murine ADA signal. On the other hand, irrelevant host cells do dilute the signal from exogenous DNA, since the genomic DNA was extracted from whole spleen tissue, and a constant amount of genomic DNA was applied to each lane. Therefore, the measure of ADA activity is independent of the number of host cells, however, the Southern blotting is affected; this explains the variation between FIG. 7A and 7B. Lymphocytes expressing the human ADA gene were also found in LN, however, the SCID LN were always small and contained very few cells (data not shown).

These results present a reproducible animal model system for the introduction and expression of exogenous genes in mature primary B cells. This model suggests that the transduction of B cells presents a viable option for the long-term expression of an exogenous gene in either the blood or the lymphoid compartment. This easy and relatively inexpensive animal model may prove appropriate for use as an initial screening procedure of different somatic cell gene therapy protocols using B cells as targets.

EXAMPLE 2

Induced Unresponsiveness in Autoimmune Disease

Plasmid constructions. Generally, DNA recombinants are made using oligonucleotide primers and PCR. The primers contain unique restriction sites to facilitate cloning. This approach allows easy isolation and cloning of fragments with precise coordinates. For PCR, the Viu DNA polymerase is used because it has been reported to yield 12-fold and 5-fold greater fidelity than Taq and Vent polymerases, respectively, owing to the Pf polymerase having 3' to 5' proofreading exonuclease activity (Strategene catalogue 1992, p. 126). Although PCR is carried out with Pfu DNA polymerase, additional steps are performed to ensure that inserted sequences do not contain mutations introduced during PCR. To do this, the amplified DNA is first cloned into a plasmid such as pUC18. For inserts 500 bp or smaller, the entire fragment can be sequenced employing standard dideoxyy sequencing. For inserts larger than 500 bp, the central portion of the PCR amplified insert is replaced with the corresponding fragment from a plasmid using whichever unique restriction sites that are available; hence only the 5' and the 3' ends need to be sequenced since only they would be products of PCR.

Retroviral vectors. Murine leukemia virus (MLV)-based retroviral vectors may be used in all experiments to introduce the desired genes into the target cells. A schematic of all the vectors to be used in these studies is presented in FIG. 8. Vectors are produced using the ecotropic packaging cell line GP+E-86 (see Example 1, supra). Packaging (helper) cell lines producing vector virus at titers of $5 \times 10^6 – 2 \times 10^7$ colony-forming units (CF) per ml (as assayed on NIH 3T3 cells) are isolated. For vectors containing the neo gene, titers are determined, and the stability of the vector after passage is analyzed by Southern blotting. For vectors that do not contain the neo gene, Southern blotting is used to determine relative titer by comparing the signal obtained after passage to that obtained with a control viral stock that yields a titer in the range of $1 \times 10^7$.

In the vectors described in FIG. 8, the spleen necrosis virus promoter is used to drive expression of the second gene. This is to be a particularly strong promoter in many cells, including murine cells. Other promoters can also be used, such as the human ADA promoter, which we have used to express efficiently human ADA in murine B and T cells (supra).

Preparation of cells and infection protocols. In all experiments, both mature B cells and pre-B cells are used as target cells for the expression of the myelin encephalitogenic determinants. Enriched populations of mature B cells are prepared by depleting whole spleen and LN cells from T cells by using a cocktail of mAB specific for Thy-1, CD4 and CD8. Such enrichment protocol yields >95% B cells from LN and 85% from spleen. For infection, B cells are stimulated for 16 hours with LPS, and then co-cultivated with lethally-irradiated helper cells for 24 hrs. LPS-induced proliferation of the target cells is required for efficient integration of the provirus. With this method, we routinely obtained an infection efficiency of 1 to 3 proviral copies per target cell genome for both splenic and LN B cells (supra).

Pre-B cells will be isolated from long-term Whitlock and Witte cultures (1982, Proc. Natl. Acad. Sci. USA 79:3608). Cells are harvested from the cultures 4–8 weeks after initiation and are expanded in vitro for 2 weeks with 50 ng/ml rIL-7 in RPMI media supplemented with 10% FCS, and 50 $\mu$M 2-mercaptoethanol. rIL-7 induces pre-B cells to proliferate, a necessary step for retrovirus infection, but it does not induce differentiation. Pre-B cells from these cultures do not reconstitute the B cell lineage in SCID mice, but they do differentiate into mature $\mu$+ and $\delta$+B cells. Both types of B cells persist for long periods of time following adoptive transfer into SCID mice. Previous studies (Ron and Sprent, 1985, J. Exp. Med. 161:1581; Sprent et al., 1991, J. Exp. Med. 174:717) have also shown that normal, mature B cells survive for many months upon transfer into normal or SCID recipients.

Assessment of infection and expression. The copy number of the introduced genes is assessed by Southern blotting using a neo-specific probe for vectors DR1–9 and with SNV-specific probes for vectors DR8 and DR10. Expression of the introduced genes is assessed by Northern blotting using probes for the relevant genes. For example, for expression from the DR1 vector, an MBP-specific probe is used. A number of MBP-specific mAbs including mAbs specific for the PLJ, SJL, and PLB-derived encephalitogenic peptides have been prepared. Using these mAbs, protein production is assessed by immunoprecipitations from total cell lysates. Fusion proteins may also be detected using these mAbs. In the event that the processed proteins can be recognized when complexed to MHC class-II molecules, expression will also be assessed by flow cytometry.

Assessment of immunologicalfunction. All of the infected B cells are assayed in vitro for their ability to induce the proliferation of purified antigen-primed LN T cells in the absence of exogenous antigen. To obtain primed T cells, mice are immunized with the relevant antigen in CFA in the footpads. LN CD4+T cells are prepared 9 days later by treatment with anti-CD8 and anti-HSA mAbs (treatment with the anti-HSA mAb J11d and complement removes practically all B cells from LN preparations). The cells are then passed over nylon wool columns and stimulated in vitro with the relevant antigen-pulsed infected B cells. The infected B cells are also assayed for induction of anergy using the same assay but with addition of exogenous antigen. These assays are only used as a rough assessment of the ability of the infected B cells to present antigen in immunogenic or tolerogenic forms.

Subsequent to the initial in vitro assays, the infected B cells are transferred into the appropriate strain of EAE-susceptible mice in doses of 20–40×10$^6$ cells, 4–10 times in weekly intervals. The recipient mice are challenged with an encephalitogenic dose of the relevant encephalitogen or with an encephalitogenic dose of encephalitogenic T cell lines prepared as previously described (Meyers et al., 1993, J. Immunol.). Infected B cells are also transferred into mice at different time points after the induction of EAE to test whether unresponsiveness can be induced after T cell expansion.

Parallel experiments also include treatments with monoclonal antimurine IL-2 antibodies. Anti-IL-2 antibodies were shown to prevent T cell activation and induction of specific unresponsiveness (Dallman et al., 1991, J. Exp. Med. 173:79; Andreu-Sanchez et al., 1991, J. Exp. Med. 173:1323). Recipients depleted of CD4 cells by anti-CD4 antibodies may also be used. Such depletion was shown to increase the sensitivity to antigen-specific tolerance induction (Vandervegt et al., 1993, J. Exp. Med. 177:1587).

Expression of the complete MBP and PLP genes or their encephalitogenic determinations in mature and pre-B cells. Usually, only proteins that enter the cell from the outside via endocytosis end up in the lysosomal compartment where they are processed and bind to MHC class II molecules. On the other hand, peptides expressed intracellularly bind predominantly to MHC class-I molecules in the ER. However, it has been reported that peptides can "cross" to the MHC class II antigen presentation pathways (Braciale and Braciale, 1991, Immunol. Today 12:124; Brodsky et al., 1991, Ann. Rev. Immunol. 9:707). Moreover, it was recently shown that 85% proteins purified from human class-II surface molecules are endogenous self proteins (Newcomb and Crosswell, 1993, J. Immunol. 150:499; Chicz et al., 1993, J. Exp. Med. 178:27). It is therefore possible that expression MBP and PLP or their corresponding encephalitogenic peptides in B cells without lysosomal targeting sequences will result in their presentation on surface class-II molecules. To test this, vectors may be constructed which will express the entire authentic MBP gene and PLP gene or minigenes encoding the encephalitogenic determinant and some flanking sequences which might assist in processing of the peptide.

The vectors encoding the complete MBP and PLP genes are DR1 and DR2, respectively. Only the coding sequences is cloned into the vector. The untranslated 5' and 3' sequences of both the MBP and PLP genes are not included in case they are involved in tissue specific expression. Instead, vector sequences will provide the 5' and 3' untranslated sequences. The MBP gene encodes 5 isoforms obtained by alternate splicing. The sequence encoding PLP (30 kD) is used in vector DR2 (FIG. 8).

Minigenes which encode a small portion of these proteins including the encephalitogenic determinants and a small stretch of flanking sequence are also constructed and placed in retroviral vectors (DR3 and DR4, FIG. 8), since the full length proteins are quite hydrophobic. The ATG start codon is placed in context of a strong translation initiation signal corresponding to that determined by Kozak (1989, J. Cell Biol. 108:229), and appropriate stop codons will be placed in all three reading frames. The various minigenes will include the two major MBP encephalitogenic determinants for H-2$^s$ (aa 87–114) or H-2$^u$ (as 1–9) or the encephalitogenic determinant for PLP (aa 139–151, with serine substitutions for cysteine).

Expression of encephalitogenic peptides as fusion proteins with lysosomal targeting proteins. Once expression of MBP, PLP or the encephalitogenic peptides is obtained in the target B cells, appropriate processing for class-II presentation, which occurs in the endosomal compartment can be facilitated. Lysosomal localization may expedite processing and binding to MHC class-II molecules. Therefore, in addition to the wild-type form, the encephalitogenic peptides are fused in-frame to proteins known to be localized to the lysosomal compartment. Three specific proteins are used to direct expression of the encephalitogenic proteins to lysosomes: a) The cytoplasmic tail of lysosomal acid phosphatase (LAP). Native LAP requires lysosomal processing before it is transferred to the cell surface. Targeting into the lysosomal compartment is conferred by a short (19 aa) cytoplasmic tail (Peters et al., 1990, EMBO J. 9:3497). A mini gene encoding a fusion protein consisting of LAP cytoplasmic tail and an encephalitogenic peptide is constructed (FIG. 8, DR5). b) The cytoplasmic tail of lysosome membrane glycoprotein lamp-1. As for LAP, the cytoplasmic tail of lamp-1 was found to direct targeting of this integral membrane glycoprotein specific to lysosomes (Williams and Fukuda, 1990, J. Cell. Biol. 111:955). A mini gene encoding a fusion protein consisting of LAP cytoplasmic tail and an encephalitogenic peptide will be constructed (FIG. 8, DR5). c) Class-II associated invariant chain (Ii) which was shown to target MCH class-II molecules to the endosomal compartment (FIG. 8, DR6; Braciale and Braciale, supra; Brodsky et al., supra; Bakke and Dobberstein, 1990, Cell 63:707). The sequences encoding encephalitogenic peptides are fused to the 3' coding sequence of these genes. Placement at the carboxyl terminus ensures that the encephalitogenic peptides will end up within the lysosome.

EXAMPLE 3

Co-Expression of an Auto Antigen and Ribozymes

Co-expression of encephalitogenicpeptides with B7-specific ribozymes. In this section procedures are described to inhibit expression of B7-1 and B7-2. B7-1 and B7-2 are cell surface molecules expressed on professional APC including activated B cells. They bind to CD28 expressed on the surface of T cells. The interaction between these two molecules leads to the transduction of a costimulatory signal which is required for productive T cell activation (Linsley et al., 1991, J. Exp. Med. 173:721; Freeman et al., 1991, J. Exp. Med. 174:625; Reiser et al., 1992, Proc. Natl. Acad. Sci. USA 89:271; Azuma et al., 1993, Nature 366:76; Freeman et al., 1993, J. Exp. Med. 178:2185; Freeman et al., 1993, Science 262:907). APC that do not express B7 molecules induce long-lasting clonal anergy rather than clonal activation (Linsley and Ledbetter, 1993, Ann. Rev. Immunol. 11:191; Schwartz, 1992, Cell 71:1065; Ding et al., 1993, J. Immunol. 151:1224; Azuma et al., supra; Freeman et al., 1993, J. Exp. Med., supra; Freeman et al., 1993, Science, supra). B cells will be infected with a retroviral vector that can express both myelin determinants and a B7-specific ribozymes.

An improvement in antisense RNA technology has evolved with the discovery of natural occurring RNA molecules capable of undergoing autolytic cleavage (Tanner and Vasseur, 1993, in Antisense research and applications, S. Crooke and B. Leblen, Eds., CRC Press, Inc.: Boca Raton, Fla., pp. 415–26). Self-catalyzed RNA cleavage was first demonstrated in the protozoan Tetrahymena thermophila, and since then has been demonstrated for a variety of molecules in bacteria, plants, and animals. A comparison of sequences of several catalytic RNAs led to the consensus structure for some of these RNA enzymes, known as ribozymes. At least some ribozymes do not need to be situated on one contiguous strand in order for them to have catalytic activity; they can be prepared from two separate RNA strands that hybridize to form a catalytic motif, so they can act in trans. The three types of trans-cleaving ribozymes that have been described are the hammerhead, the hairpin, and the hepatitis delta virus (HDV) ribozymes. RNA cleavage by these ribozymes results in termini consisting of a 2,3' cyclic phosphate and a 5'-hydroxyl. Truncation experiments of hairpin and hammerhead ribozymes have demonstrated that as little as fifty nucleotides are required for catalytic activity whereas for the HDV ribozyme 85 nucleotides are required. Although the substrate requirement for the HDV ribozyme is not well defined at this time, it is known for the hammerhead and hairpin ribozymes. For the hammerhead and hairpin ribozymes, the substrate requirement is minimal. For the hammerhead ribozyme it is dictated only by a GUX 5' to the site of cleavage where X cannot be a G, and for the hairpin ribozyme, it is dictated by a GUC 3' to the cleavage site. These observations allow for highly specific ribozymes to be designed by the inclusion of antisense RNA extensions that hybridize to the target RNA in the 5' and 3' directions from the catalytic site. The antisense portion of the ribozyme typically range from 12 to 20 nucleotides. Moreover, since ribozymes possess catalytic activity, they should be able to cleave multiple substrate RNAs without being consumed which is important for their potential effectiveness.

Two particularly important technical considerations apply when considering the use of ribozymes. They are the accessibility of the target RNA and the intracellular concentration of the ribozyme. The vectors that will be constructed and tested directly address these potential problems. DR7, DR8, and DR9 are vectors designed to utilize the ability of ribozyme containing vectors to inhibit the expression of B7 proteins.

DR7 (FIG. 8) contains a multivalent ribozyme directed against both B7-1 and B7-2. The ribozyme contains two specificities. One is a hammerhead ribozyme directed against B7-1 (coordinates 509 to 528). The antisense portion of the ribozyme hybridizes to 12 nucleotides 5' and 8 nucleotides 3' to the site of cleavage. The second is a hairpin ribozyme specific for B7-2 (coordinates 362 to 381), and its antisense portion is also 20 nucleotides in length. It is noteworthy that multivalent ribozymes, including nonaribozymes, have already been described (Chen et al, 1992, Nucl. Acid. Res. 20:4581–9). Both hammerhead and hairpin ribozymes are being used because we wish to avoid introducing direct repeats into the retroviral vectors since or laboratory and other shave noted that direct repeats in a retrovirus can lead to high rates of deletion even after a single cycle of retroviral replication.

In vector DR7, the ribozyme found on at least two transcripts, the full-length transcript initiated from the LT promoter, and the subgenomic transcript initiated from the SNV promoter. The larger transcript initiated from the LT promoter encodes neomycin phosphotransferase. A strategy wherein the ribozyme is included a part of a coding RNA is believed to be important because a potential problem in obtaining high concentrations of the ribozyme is that a mechanism has evolved in cells that degrades noncoding mRNAs (Leeds et al., 1991, Genes & Develop., 58:2303–14). It has been demonstrated that transcripts containing nonsense mutations, which are equivalent to noncoding mRNAs, have dramatically reduced mRNA levels in cells (Pellts and Jacobson, 1993, In Control of messenger RNA stability, Academic Press, Inc., pp. 291–328). Premature termination of translation by either nonsense or frameshift mutations promotes rapid degradation of a variety of mRNAs. Antisense RNAs, which are noncoding RNAs, also might be degraded via this mRNA turnover pathway. Since the antisense RNA is not meant to encode a gene product, any time translation initiation occurs on the antisense RNA, it will most likely lead to rapid translation termination and degradation unless it is located in the 3' noncoding region of a coding mRNA.

DR7 is subjected to two tests before using the vector in primary B cells.

(a) First it is ascertained whether the ribozymes cleave substrate RNAs in a cell-free system. Recombinants are constructed with the T7 promoter to enable production of in vitro transcripts of both the bivalent ribozyme and substrate V7-1 and B7-2 RNAs. Standard in vitro cleavage reactions are performed, and the substrate analyzed by gel electrophoresis and autoradiography according to already descried protocols (Chen et al., supra; Dropulic et al., 1992, J. Virol. 66:1432–41; Weerasinge et al., 1991, J. Virol. 65:5531–4). Ribozymes directed against different portions of B7-1 and B7-2 can also be made and tested.

(b) Since the ribozymes should significantly reduce B7-1 and B7-2 RNA levels in vector infected cells, this can be analyzed by Northern blotting. A B16 murine melanoma cell line transfected with expression plasmids expressing both B7-1 and B7-2 (the cell line is designated B17-B7) is used. After infection of B17-B7 cells with DR7 and selection in media containing G418, RNA is isolated and analyzed via Northern blotting. RNA from mock-infected B17-B7 cells is included as a control. Effective expression and action of the ribozyme should result in a significant decrease in steady-state levels of both B7 RNAs.

In the second type of vector (DR8, FIG. 8), an RNA sequence which forms an intramolecular duplex preventing translation is inserted 5' to the bivalent ribozyme. The idea behind this is to prevent translation of the noncoding ribozyme mRNA in order to abrogate its decay and increase its steady-state levels. The sequence that will be added was originally described by Kozak (1989, Mol. Cell. Biol. 9:5134–42), and it forms a stem-loop structure which prevents formation of translation initiation complexes, when it is present at the 5' end of a transcript. Before use in primary B cells, testing of the vector may be performed as described above. In addition, the steady-state levels of subgenomic RNA expressed from the SNV promoter of DR8 can be compared to that obtained with DR9 to determine whether ribozyme RNA was further stabilized by inclusion of the stem-loop structure.

In the third type of vector (DR9, FIG. 8), a gene is constructed that should produce a dual functional mRNA capable of encoding both a protein to augment clonal anergy and a ribozyme capable of degrading B7 RNAs. More specifically, the bivalent ribozyme specific for the B7 RNAs is inserted into the 3' noncoding portion of the IL-10 gene. How IL-1 can augment induction of clonal anergy is discussed in the next section. This serves three purposes: a) the ribozyme becomes linked to a coding sequence which should serve to stabilize the ribozyme and increase its steady-state levels, b) this RNA containing the ribozyme should be translated by ribosomes of the rough endoplasmic reticulum just a the B7 RNAs, so this should ensure that both RNAs are localized to the same subcellular compartment increasing the likelihood of efficient actio of the ribozyme, and c) it creates a single gene potentially capable of expressing products that can augment induction of clonal anergy at two different levels. Again before proceeding to primary B cells, tests of DR9 efficacy will be done as described for vector DR8. Additionally, infected B16-B cells will also be assayed for IL-10 expression, which is explained in more detail in the next section.

EXAMPLE 4

Co-Expression of Encephalitogenic Peptides with IL-10

IL-10 is a cytokine produced by macrophages, B cells and mainly by TH2 cells (Howard and O'Garra, 1992, Immunol. Today, 13:198; Moore et al., 1993, Ann. Rev. Immunol., 11:165). It was originally described as an inhibitor of THI cells and it was later found that it acts by blocking cytokine production by APC. It has many other effects on various hematopoietic cells. For example, it was shown to enhance B cell viability, induce expression of class-II antigens and to synergize with IL-4 to induce B cell proliferation. Its inhibitory function on macrophages was recently shown to be due to the selective inhibition of the up-regulation of B7 expression during APC activation (Ding et al., 1993, Immunol. 15:1224). Therefore, constitutive co-expression of IL-10 with the encephalitogenic determinants from the same vector should inhibit the activation of TH1 cells and therefore might be led to the induction of clonal anergy without the use of B7-specific ribozymes. To express IL-10, the vector DR10 (first without the inclusion of ribozymes) is constructed. The entire coding sequence of IL-10 (17 kD in the absence of N-linked glycosylation) is inserted into this vector and expressed from the MLV LTR promoter. The genes coding for the encephalitogenic determinants are expressed from the SNV promoter.

The B7-specific ribozymes may be included in DR10 in the 3' untranslated portion of the IL-10 gene. If both the strategies (ribozymes and IL-10) prove to work in concern, DR10 would obviously be the preferred vector to use in primary B cells. Secretion of IL-10 will be detected with the rat monoclonal antibody SXCI using ELISA and by induction of proliferation of the indicator line MC-9. This cell line responds to IL-10 when stimulated with suboptimal doses (0.25 ng/ml) of murine IL-4.

Throughout this application, various publications have been referenced. The disclosures in these publications are incorporated herein by reference in order to more fully describe the state of the art.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method for introducing a gene encoding a myelin encephalitogenic determinant into primary lymphoid cells without drug selection, comprising the steps of:
    a) stimulating a selected lymphoid subpopulation with growth factors that induce proliferation of the lymphoid subpopulation for a time sufficient to induce proliferation of the lymphoid subpopulation; and
    b) co-culturing the stimulated lymphoid subpopulation with a virus-producing helper cell line harboring a retroviral vector carrying a gene encoding a myelin encephalitogenic determinant, wherein the level of virus production of the helper cell line is in the range from $5 \times 10^6$ to $5 \times 10^7$ colony forming units/ml.

2. The method according to claim 1, wherein the virus-producing cell line is prepared by transfecting a vector into a producer cell followed by selection, isolation of cell clones, and determination of viral titers to identify which virus-producing cell lines produce a virus titer in the range from $5 \times 10^6$ to $5 \times 10^7$ units/ml.

3. The method according to claim 1, wherein the selected lymphoid subpopulation is depleted of undesired cells.

4. The method according to claim 1, wherein the lymphoid subpopulation is capable of repopulating a specific lymphoid lineage, or a long-lived population.

5. The method according to claim 1, wherein the lymphoid cells are primary, mature lymph node T and B cells or primary, immature CD4-CD8-double-negative (DN) thymocytes.

6. The method according to claim 1, wherein the retroviral vector is pN2 or pAsADA Moloney murine leukemia virus (MLV)-based retroviral vectors.

7. The method according to claim 1, wherein the producer cell is the GP+E-86 cell line.

8. The method according to claim 1 wherein greater than 90% of the primary lymphoid cells harbor one or more provirus vectors carrying the gene encoding a myelin encephalitogenic determinant.

9. The method according to claim 1, wherein the myelin encephalitogenic determinant is selected from the group consisting of myelin basic protein, proteolipid protein, a portion of myelin basic protein containing the encephalogenic determinant, and a portion of the proteolipid protein containing the encephalogenic determinant.

10. The method according to claim 1, wherein the gene encoding a myelin encephalitogeic determinant is expressed from a spleen necrosis virus promoter.

11. The method according to claim 1, wherein the gene encoding a myelin encephalitogeic determinant fused with a lysosomal or endosomal targeting protein gene.

12. The method according to claim 3, wherein the depletion of undesired cells is achieved by treating a suspension of lymphoid cells with a polyclonal or a monoclonal antibody and complement, by panning, by nylon wool selection, or by differential gradient centrifugation.

13. A population of lymphocytes, wherein greater than 90% of the lymphocytes harbor one or more provirus vectors carrying a gene encoding a myelin encephalitogenic determinant.

14. The population of lymphocytes of claim 13, wherein the lymphocytes are selected from the group consisting of mature B cells, mature T cells, immature B cells, and immature T cells.

15. The population of lymphocytes of claim 13, wherein the myelin encephalitogenic determinant is selected from the group consisting of myelin basic protein, proteolipid protein, a portion of myelin basic protein containing the encephalogenic determinant, and a portion of the proteolipid protein containing the encephalogenic determinant.

16. The population of lymphocytes of claim 13, wherein the gene encoding a myelin encephalitogeic determinant is expressed from a spleen necrosis virus promoter.

17. The population of lymphocytes of claim 13, wherein the gene encoding a myelin encephalitogeic determinant fused with a lysosomal or endosomal targeting protein gene.

18. The method according to claim 9, wherein the gene encoding a myelin encephalitogeic determinant is expressed from a spleen necrosis virus promoter.

19. The method according to claim 9, wherein the gene encoding a myelin encephalitogeic determinant fused with a lysosomal or endosomal targeting protein gene.

20. The method according to claim 11, wherein the lysosomal or endosomal targeting protein is selected from the group consisting of the cytoplasmic tail of lysosomal acid phosphatase, the cytoplasmic tail of lysosome membrane glycorotein lamp-1, and the class-II associated invariant chain.

21. The method according to claim 19, wherein the lysosomal or endosomal targeting protein is selected from the group consisting of the cytoplasmic tail of lysosomal acid phosphatase, the cytoplasmic tail of lysosome membrane glycorotein lamp-1, and the class-II associated invariant chain.

22. The population of lymphocytes of claim 15, wherein the gene encoding a myelin encephalitogeic determinant is expressed from a spleen necrosis virus promoter.

23. The population of lymphocytes of claim 15, wherein the gene encoding a myelin encephalitogeic determinant fused with a lysosomal or endosomal targeting protein gene.

24. The population of lymphocytes of claim 17, wherein the lysosomal or endosomal targeting protein is selected from the group consisting of the cytoplasmic tail of lysosomal acid phosphatase, the cytoplasmic tail of lysosome membrane glycorotein lamp-1, and the class-II associated invariant chain.

25. The population of lymphocytes of claim 23, wherein the lysosomal or endosomal targeting protein is selected from the group consisting of the cytoplasmic tail of lysosomal acid phosphatase, the cytoplasmic tail of lysosome membrane glycorotein lamp-1, and the class-II associated invariant chain.

26. A retroviral vector comprising a retroviral long terminal repeat at the 5' and 3' ends, and a gene encoding a myelin encephalitogenic determinant expressed from a promoter.

27. The vector of claim 26, wherein the myelin encephalitogenic determinant is selected from the group consisting of myelin basic protein, proteolipid protein, a portion of myelin basic protein containing the encephalogenic determinant, and a portion of the proteolipid protein containing the encephalogenic determinant.

28. The vector of claim 26, wherein the promoter is a spleen necrosis virus promoter.

29. The vector of claim 26, wherein the gene encoding a myelin encephalitogeic determinant is fused with a lysosomal or endosomal targeting protein gene.

30. The vector of claim 29, wherein the lysosomal or endosomal targeting protein is selected from the group consisting of the cytoplasmic tail of lysosomal acid phosphatase, the cytoplasmic tail of lysosome membrane glycoprotein lamp-1, and the class-II associated invariant chain.

* * * * *

UNITED STATES PATENT AND TRADEMARK OFFICE
CERTIFICATE OF CORRECTION

PATENT NO.    : 5,906,928
DATED         : May 25, 1999
INVENTOR(S)   : Joseph Dougherty; Yacov Ron; Chiann Chyi Chen; and Amariliz Rivera Page 1 of 1

It is certified that error appears in the above-identified patent and that said Letters Patent is hereby corrected as shown below:

Please add the following two (2) co-inventors on the title page:

-- Chiann Chyi Chen, Piscataway, NJ; Amariliz Rivera, Piscataway, NJ --

Signed and Sealed this

Twenty-third Day of October, 2001

Attest:

*Nicholas P. Godici*

NICHOLAS P. GODICI
*Acting Director of the United States Patent and Trademark Office*

*Attesting Officer*

UNITED STATES PATENT AND TRADEMARK OFFICE
CERTIFICATE OF CORRECTION

PATENT NO.    : 5,906,928
DATED         : May 25, 1999
INVENTOR(S)   : Joseph Dougherty et al.

It is certified that error appears in the above-identified patent and that said Letters Patent is hereby corrected as shown below:

<u>Column 1,</u>
Line 4, add the following paragraph after the Title:

-- GOVERNMENT RIGHTS

The research leading to the present invention was supported, in part, by the following grants from the National Institute of Health: CA50777 and AI 07043. Accordingly, the United States Government may have certain rights in the invention. --

Signed and Sealed this

Fifteenth Day of July, 2003

JAMES E. ROGAN
*Director of the United States Patent and Trademark Office*